US011273103B1

(12) United States Patent      (10) Patent No.: US 11,273,103 B1
Brakkee et al.      (45) Date of Patent: Mar. 15, 2022

(54) METHOD, COMPUTER PROGRAM PRODUCT AND DISPENSING DEVICE FOR DISPENSING DISCRETE MEDICAMENTS

(71) Applicant: VMI Holland B.V., Epe (NL)

(72) Inventors: Martinus Johannes Donatus Brakkee, Epe (NL); Peter Van Roon, Epe (NL); Patrick Van Voorn, Epe (NL)

(73) Assignee: VMI Holland B.V., Epe (NL)

( * ) Notice: Subject to any disclaimer, the term of this patent is extended or adjusted under 35 U.S.C. 154(b) by 0 days.

(21) Appl. No.: 17/353,986

(22) Filed: Jun. 22, 2021

(51) Int. Cl.
| | |
|---|---|
| *G06F 7/00* | (2006.01) |
| *A61J 7/00* | (2006.01) |
| *B65G 1/10* | (2006.01) |
| *B65B 5/10* | (2006.01) |
| *B25J 11/00* | (2006.01) |
| *B65G 1/04* | (2006.01) |

(52) U.S. Cl.
CPC .............. *A61J 7/0084* (2013.01); *B25J 11/00* (2013.01); *B65B 5/103* (2013.01); *B65G 1/045* (2013.01); *B65G 1/10* (2013.01)

(58) Field of Classification Search
CPC ......... A61J 7/0084; B25J 11/00; B65B 5/103; B65G 1/045; B65G 1/10
USPC ...................................................... 221/1, 21
See application file for complete search history.

(56) References Cited

U.S. PATENT DOCUMENTS

| | | | |
|---|---|---|---|
| 2,012,405 | A | 8/1935 | Salfisberg |
| 2,786,566 | A | 3/1957 | Taggart et al. |
| 3,409,721 | A | 11/1968 | Applezweig |
| 3,871,156 | A | 3/1975 | Koenig et al. |
| 3,925,960 | A | 12/1975 | Saari et al. |
| 4,065,000 | A | 12/1977 | Murton |
| 4,101,284 | A | 7/1978 | Difiglio et al. |
| 4,542,808 | A | 9/1985 | Lloyd, Jr. et al. |
| 5,219,095 | A | 6/1993 | Shimizu et al. |
| 5,481,855 | A | 1/1996 | Yuyama |
| 5,481,885 | A | 1/1996 | Xavier et al. |
| 5,549,217 | A | 8/1996 | Benarrouch |
| 5,678,393 | A | 10/1997 | Yuyama et al. |
| 5,865,342 | A | 2/1999 | Ito et al. |

(Continued)

FOREIGN PATENT DOCUMENTS

| | | |
|---|---|---|
| AU | 2014301427 A1 | 2/2016 |
| AU | 2016339741 A1 | 5/2018 |

(Continued)

*Primary Examiner* — Yolanda R Cumbess
(74) *Attorney, Agent, or Firm* — N.V. Nederlandsch Octrooibureau; Catherine A. Shultz; Katelyn J. Bernier

(57) ABSTRACT

A method, a computer program product and a dispensing device for dispensing discrete medicaments,
wherein the dispensing device comprises a dispensing section, a collection section and a packaging section, wherein the dispensing section defines an array of feeder positions for holding a plurality of feeder units, wherein the collection section comprises a first collection unit that is movable in a collection direction,
wherein the method comprises the steps of:
   positioning a first feeder unit at a first feeder position; and
   prior to removing the first feeder unit from the first feeder position, positioning a second feeder unit at a second feeder position, downstream from the first feeder position in the collection direction,
wherein the first feeder unit and the second feeder unit hold medicaments of the same first composition.

24 Claims, 11 Drawing Sheets

(56) References Cited

U.S. PATENT DOCUMENTS

| | | |
|---|---|---|
| 5,908,113 A | 6/1999 | Takemasa et al. |
| 5,934,048 A | 8/1999 | Bouressa |
| 6,006,946 A | 12/1999 | Mckesson |
| 6,011,998 A | 1/2000 | Lichti et al. |
| 6,036,812 A | 3/2000 | Williams et al. |
| 6,073,799 A | 6/2000 | Yuyama et al. |
| 6,170,699 B1 | 1/2001 | Kim |
| 6,199,698 B1 | 3/2001 | Hetrick et al. |
| 6,208,911 B1 | 3/2001 | Yamaoka et al. |
| 6,216,418 B1 | 4/2001 | Kim |
| 6,367,232 B2 | 4/2002 | Kim |
| 6,385,943 B2 | 5/2002 | Yuyama |
| 6,481,180 B1 | 11/2002 | Takahashi et al. |
| 6,625,952 B1 | 9/2003 | Chudy et al. |
| 6,792,736 B1 | 9/2004 | Takahashi et al. |
| 7,017,623 B2 | 3/2006 | Tribble et al. |
| 7,182,105 B1 | 2/2007 | Feehan et al. |
| 7,289,879 B2 | 10/2007 | William et al. |
| 7,493,744 B2 | 2/2009 | Nishimura et al. |
| 7,637,078 B2 | 12/2009 | Ishiwatari et al. |
| 7,784,244 B2 | 8/2010 | Siegel |
| 7,818,947 B2 | 10/2010 | Kim |
| 7,848,846 B2 | 12/2010 | Uema et al. |
| 7,856,794 B2 | 12/2010 | Zieher |
| 7,922,037 B2 | 4/2011 | Ohmura et al. |
| 7,950,206 B2 | 5/2011 | Knoth |
| 7,956,623 B2 | 6/2011 | Bassani et al. |
| 8,060,248 B1 | 11/2011 | Boyer et al. |
| 8,180,484 B2 | 5/2012 | Baker et al. |
| 8,186,542 B2 | 5/2012 | Kobayashi et al. |
| 8,220,224 B2 | 7/2012 | Ishiwatari et al. |
| 8,234,838 B2 | 8/2012 | Yasunaga et al. |
| 8,380,346 B2 | 2/2013 | Chudy et al. |
| 8,413,410 B2 | 4/2013 | Ulm et al. |
| 8,436,291 B2 | 5/2013 | Owen et al. |
| 8,511,478 B2 | 8/2013 | Terzini |
| 8,571,708 B2 | 10/2013 | Rob et al. |
| 8,678,197 B2 | 3/2014 | Koike et al. |
| D702,273 S | 4/2014 | Kim |
| 8,739,499 B2 | 6/2014 | Yasunaga et al. |
| 8,950,166 B2 | 2/2015 | Feehan et al. |
| 9,002,510 B2 | 4/2015 | Chudy et al. |
| 9,037,285 B2 | 5/2015 | Vollm et al. |
| D806,261 S | 12/2017 | Azoulay et al. |
| 9,839,583 B2 | 12/2017 | Kim |
| 9,914,554 B2 | 3/2018 | Lokkers et al. |
| 10,173,830 B2 | 1/2019 | 'T Lam et al. |
| 10,219,984 B2 | 3/2019 | Longley et al. |
| 10,252,826 B2 | 4/2019 | Lokkers et al. |
| 10,457,473 B2 | 10/2019 | Daniels et al. |
| 10,589,883 B2 | 3/2020 | Van Wijngaarden et al. |
| 2001/0001358 A1 | 5/2001 | Yuyama et al. |
| 2003/0226852 A1 | 12/2003 | Kobayashi |
| 2004/0124115 A1 | 7/2004 | Nishimura et al. |
| 2004/0188456 A1 | 9/2004 | Arai et al. |
| 2005/0224511 A1 | 10/2005 | Kim |
| 2006/0076077 A1 | 4/2006 | Kaplan et al. |
| 2009/0039899 A1 | 2/2009 | Bassani et al. |
| 2009/0045214 A1 | 2/2009 | Kobayashi et al. |
| 2009/0210247 A1 | 8/2009 | Chudy et al. |
| 2009/0211198 A1 | 8/2009 | McErlean et al. |
| 2010/0050570 A1 | 3/2010 | Mori et al. |
| 2011/0250389 A1 | 10/2011 | Paul et al. |
| 2012/0159908 A1 | 6/2012 | Hatsuno et al. |
| 2012/0324829 A1 | 12/2012 | Omura et al. |
| 2013/0270291 A1 | 10/2013 | Omura et al. |
| 2014/0318086 A1 | 10/2014 | Ishizuka |
| 2014/0366489 A1 | 12/2014 | Scholten et al. |
| 2015/0127145 A1* | 5/2015 | Kim .................. G07F 17/0092 700/235 |
| 2015/0175282 A1* | 6/2015 | Thompson ............. B65B 35/06 221/1 |
| 2015/0239585 A1 | 8/2015 | Weigel et al. |
| 2015/0339875 A1* | 11/2015 | Yasunaga ................ B65B 5/103 221/123 |
| 2016/0151244 A1 | 6/2016 | Hellenbrand |
| 2018/0290775 A1 | 10/2018 | Gross |
| 2020/0402632 A1 | 12/2020 | van Schelven et al. |
| 2021/0205179 A1* | 7/2021 | Amano .................. G16H 70/40 |

FOREIGN PATENT DOCUMENTS

| | | |
|---|---|---|
| AU | 2018249339 A1 | 10/2019 |
| AU | 2016247382 B2 | 12/2020 |
| CA | 2629632 C | 6/2013 |
| DE | 102010028568 A1 | 11/2011 |
| EM | 001349419-0001 A1 | 12/2012 |
| EM | 001453104-0001 A1 | 12/2016 |
| EP | 714651 A1 | 6/1996 |
| EP | 761197 B1 | 7/2001 |
| EP | 1114634 A2 | 7/2001 |
| EP | 760234 B1 | 11/2001 |
| EP | 1167248 A1 | 1/2002 |
| EP | 714651 B1 | 2/2003 |
| EP | 1477403 A1 | 11/2004 |
| EP | 1776275 B1 | 3/2009 |
| EP | 2098453 A1 | 9/2009 |
| EP | 1477403 A4 | 11/2009 |
| EP | 2135595 A1 | 12/2009 |
| EP | 2168879 A2 | 3/2010 |
| EP | 2450855 A2 | 5/2012 |
| EP | 2450855 A3 | 5/2012 |
| EP | 2450856 A2 | 5/2012 |
| EP | 2450856 A3 | 5/2012 |
| EP | 2450857 A2 | 5/2012 |
| EP | 2450857 A3 | 5/2012 |
| EP | 2093722 B1 | 5/2013 |
| EP | 2082718 B1 | 7/2013 |
| EP | 2098453 B1 | 7/2013 |
| EP | 2168879 A3 | 7/2015 |
| JP | H03162204 A | 7/1991 |
| JP | H0472115 A | 3/1992 |
| JP | H05132007 A | 5/1993 |
| JP | H08301301 A | 11/1996 |
| JP | H0956784 A | 3/1997 |
| JP | H09142401 A | 6/1997 |
| JP | 2798689 B2 | 9/1998 |
| JP | 3895989 B2 | 8/2001 |
| JP | 2002291845 A | 10/2002 |
| JP | 2002347702 A | 12/2002 |
| JP | 2003000677 A | 1/2003 |
| JP | 2003512088 A | 4/2003 |
| JP | 2003516279 A | 5/2003 |
| JP | 2004051230 A | 2/2004 |
| JP | 2006204495 A | 8/2006 |
| JP | 3933333 B2 | 6/2007 |
| JP | 4097760 B2 | 6/2008 |
| JP | 4338371 B2 | 10/2009 |
| JP | 2010195415 A | 9/2010 |
| JP | 2010260619 A | 11/2010 |
| JP | 2012188126 A | 10/2012 |
| JP | 2016504241 A | 5/2014 |
| JP | 2014113524 A | 6/2014 |
| KR | 20040055585 A | 6/2004 |
| KR | 20040099106 A | 11/2004 |
| KR | 20050117426 A | 12/2005 |
| KR | 20100036947 A | 4/2010 |
| WO | 9404415 A1 | 3/1994 |
| WO | 2007092093 A2 | 8/2007 |
| WO | 2012070643 A1 | 5/2012 |
| WO | 2014051281 A1 | 4/2014 |
| WO | 2015068973 A1 | 5/2015 |
| WO | 2018068798 A1 | 4/2018 |
| WO | 2019170685 A1 | 9/2019 |
| WO | 2019195629 A1 | 10/2019 |

* cited by examiner

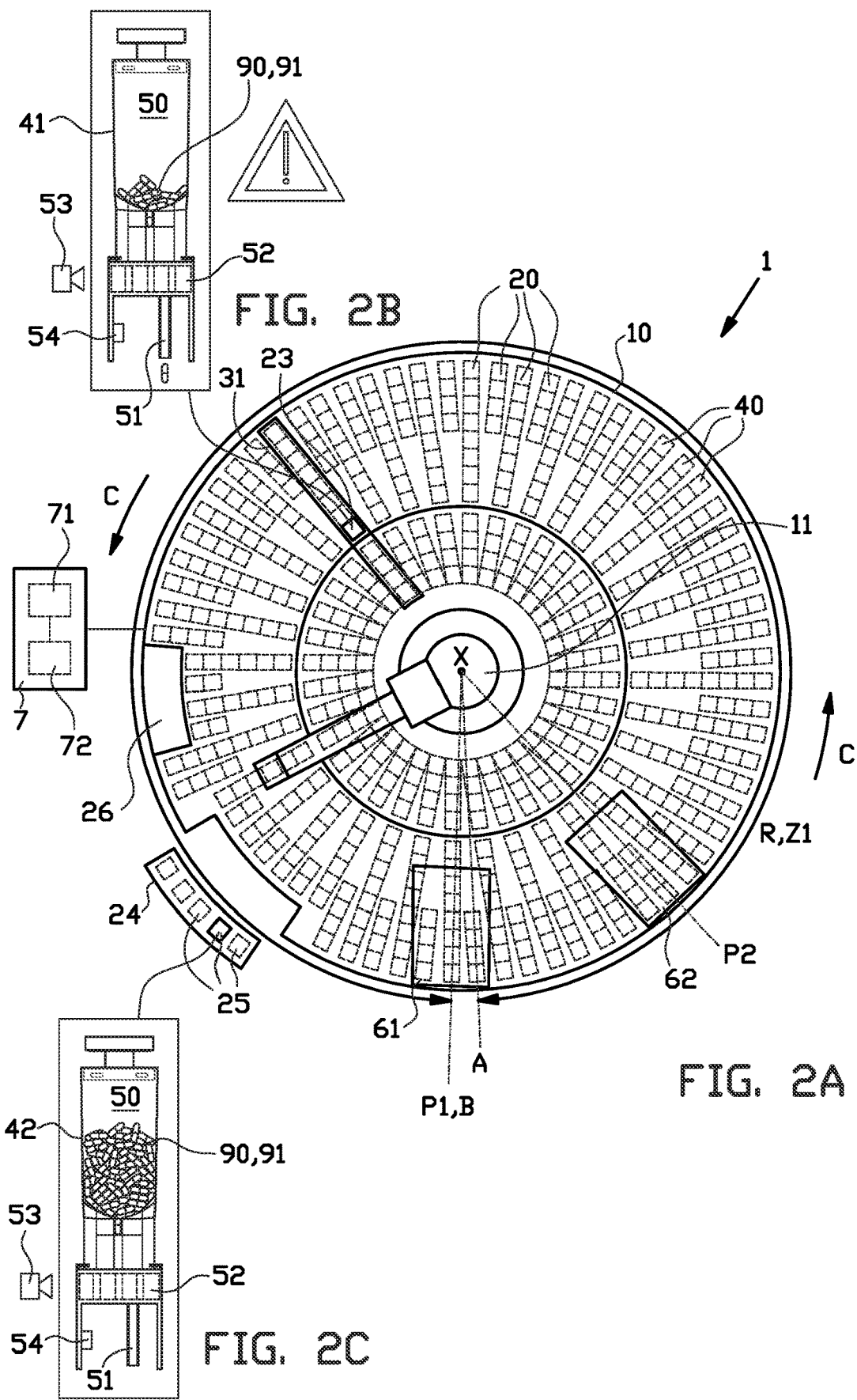

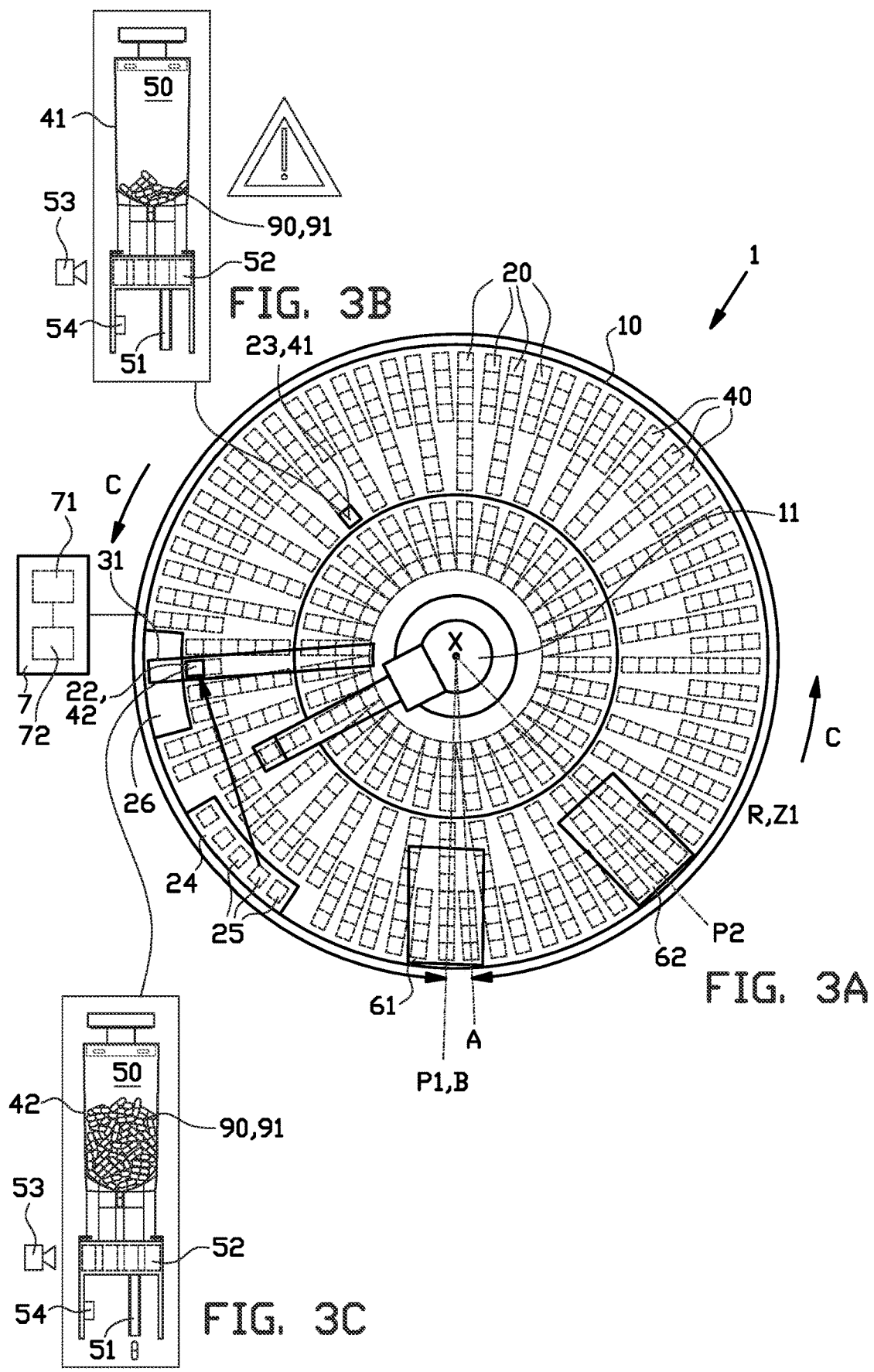

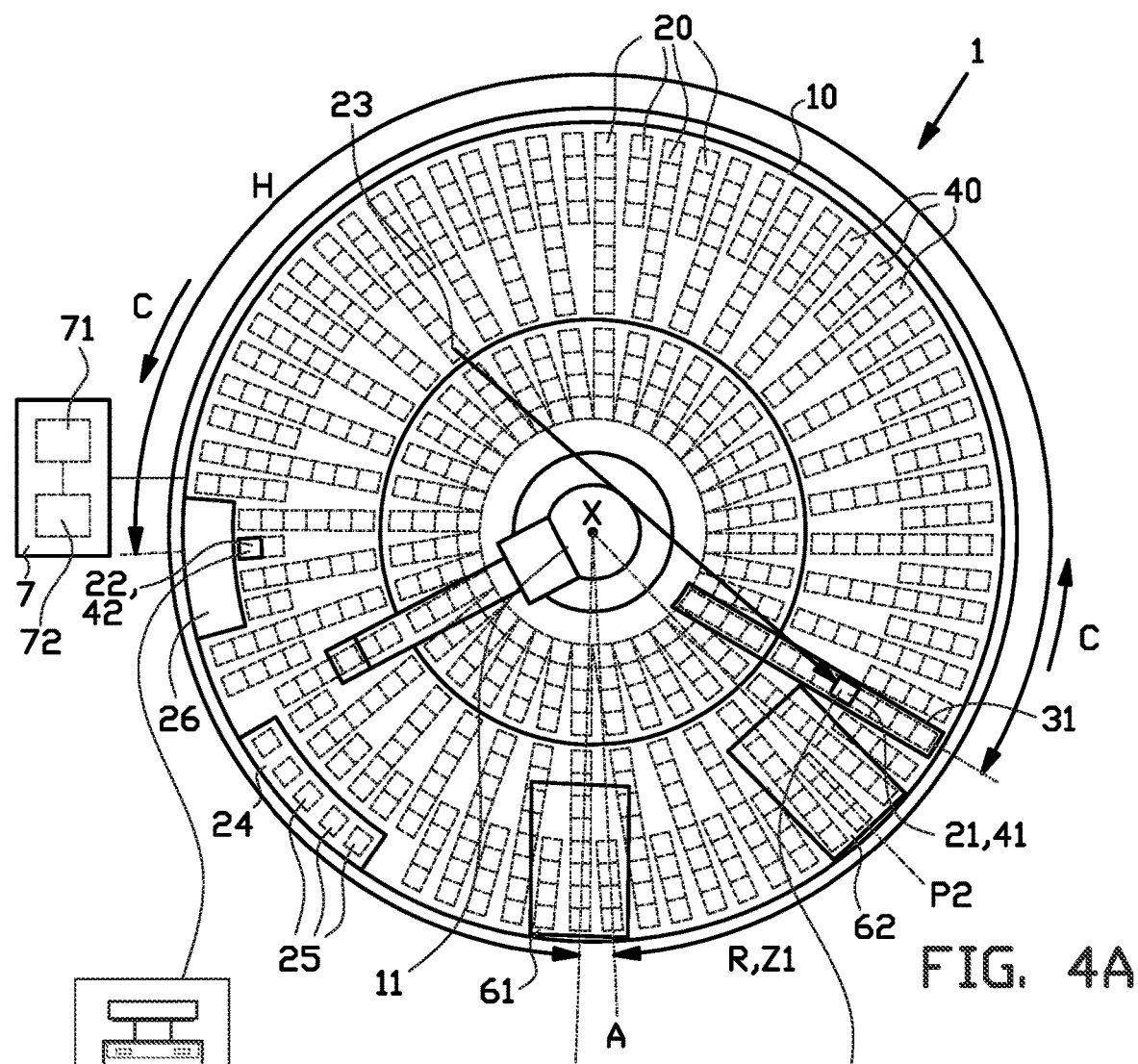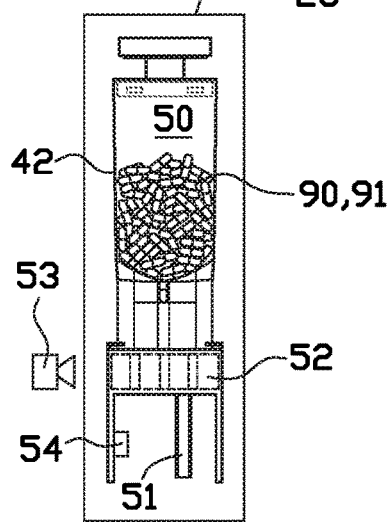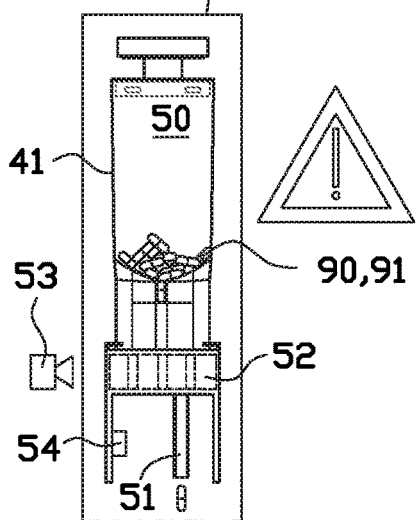

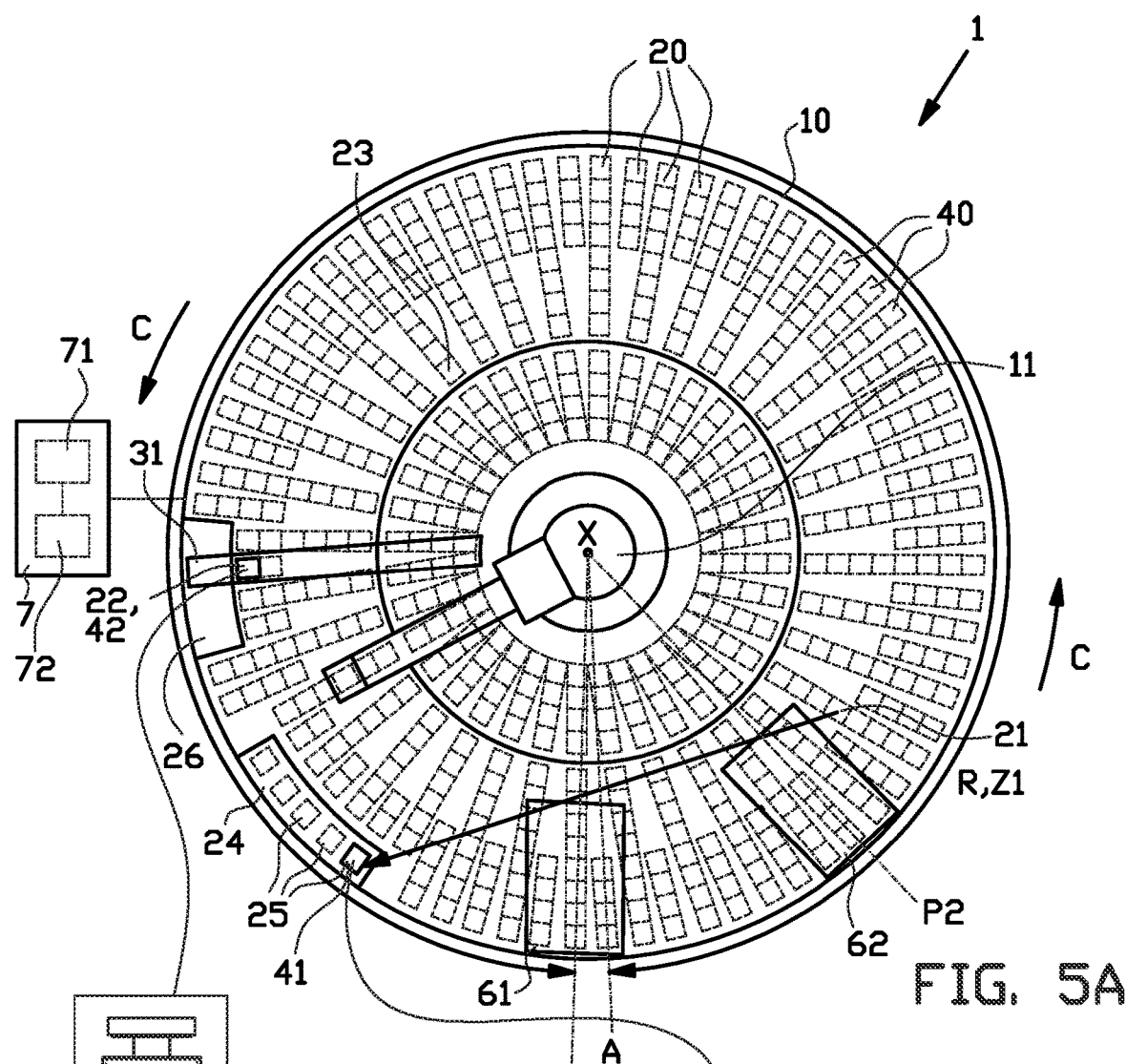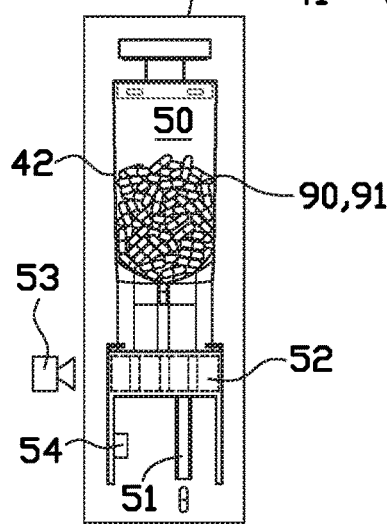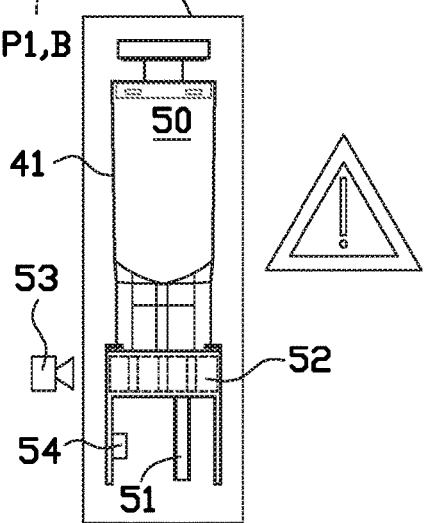
FIG. 5A
FIG. 5B
FIG. 5C

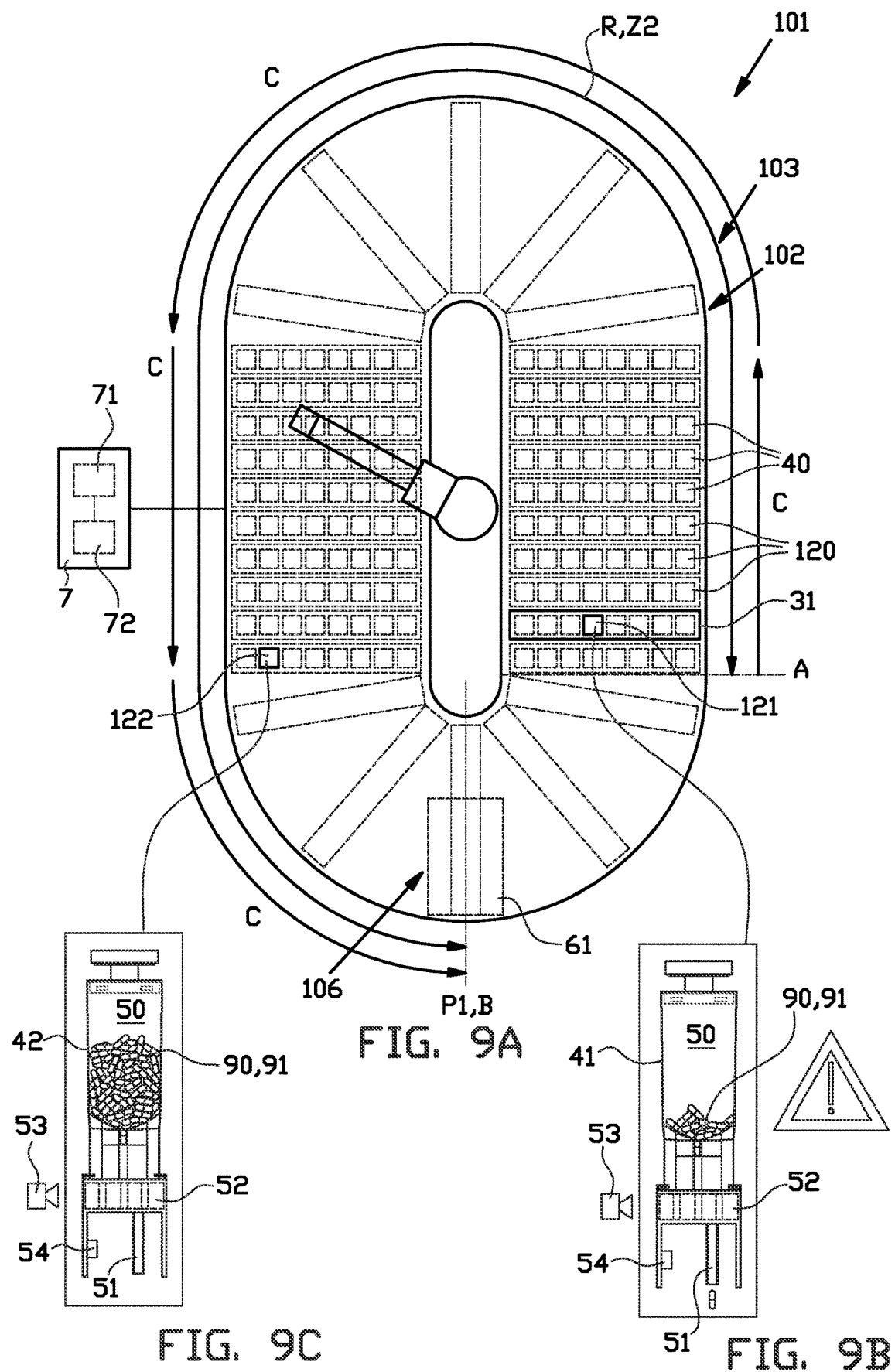

METHOD, COMPUTER PROGRAM PRODUCT AND DISPENSING DEVICE FOR DISPENSING DISCRETE MEDICAMENTS

BACKGROUND

The invention relates to a method, a computer program product and a dispensing device for dispensing discrete medicaments such as pharmaceuticals, medicaments, pills, tablets or capsules for medical use.

US 2014/0366489 A1 discloses a device for dispensing solid substances for medical use. The device is provided with a great number of feeder units, also known as 'canisters', distributed in a radial grid about a rotation axis. Each feeder unit holds an amount of solid substances specific to that respective feeder unit. Hence, together, the feeder units can dispense a wide variety of solid substances.

The device is further provided with a collection frame that is rotatable about the rotation axis below the array of feeder positions. The collection frame is provided with a series of collection trays for collecting solid substances dispensed from any of the feeder units in the array of feeder positions.

The device further comprises a packing unit arranged in a stationary position below the collection frame for packing the solid substances received from the collection trays. The collection frame is rotated about the rotation axis such that each collection tray passes along each of the feeder units in the array of feeder positions before arriving at the packing unit.

SUMMARY OF THE INVENTION

The device known from US 2014/0366489 A1 is great at continuously dispensing, collecting and packing solid substances as long as the feeder units are reliably dispensing said solid substances. However, when one of the feeder units is unexpectedly unable to dispense solid substances, for example because the solid substances held in said respective feeder unit have been depleted, when the remaining solid substances are not easily dispensed for some reason or when the remaining solid substances are past their expiry date, the dispensing is interrupted.

Automated checks or actions, such as repeated dispensing attempts and/or shaking, may be performed to make sure that the respective feeder unit is actually empty. Depending on the outcome of the checks, the human operator is informed to take appropriate action, e.g. to provide a full feeder unit to replace the empty feeder unit. The checks and the human intervention consume valuable time in which the dispensing operation of the device is interrupted. Moreover, there may be several feeder units that have to be replaced at the same time, causing even more downtime.

It is an object of the present invention to provide a method, a computer program product and a dispensing device for dispensing discrete medicaments, wherein the continuity of the dispensing operation can be improved.

A first aspect provides a method for dispensing discrete medicaments with a dispensing device,
wherein the dispensing device comprises a dispensing section, a collection section and a packaging section, wherein the dispensing section defines an array of feeder positions distributed circumferentially along an endless collection path for holding a plurality of feeder units, wherein the collection section comprises a first collection unit that is movable with respect to the array of feeder positions in a collection direction along the endless collection path between a start position downstream of a first packing position in the collection direction and an end position at or near the first packing position,
wherein the method comprises the steps of:
positioning a first feeder unit of the plurality of feeder units at a first feeder position of the array of feeder positions; and
prior to removing the first feeder unit from the first feeder position, positioning a second feeder unit of the plurality of feeder units at a second feeder position of the array of feeder positions, downstream from the first feeder position in the collection direction,
wherein the first feeder unit and the second feeder unit hold medicaments of the same first composition.

The first feeder unit may be empty earlier than expected, e.g. because of inaccurate filling, or unable to dispense any remaining medicaments. To prevent interruption of the dispensing operation when such a situation occurs, the second feeder unit can be on 'hot standby' for the first feeder unit, dispensing the medicaments of the first composition that were originally intended to be dispensed by the first feeder unit. In other words, the second feeder unit is ready to take over the dispensing operation from the first feeder unit when said first feeder unit no longer dispenses the required medicaments of the first composition. Because of the relative positioning of said second feeder unit downstream from the first feeder unit, the first collection unit does not have to wait or be moved backwards. Instead, the first collection unit can still receive the missing medicaments of the first composition from the second feeder unit while continuing the movement in the collection direction. More importantly, the first collection unit can do so prior to reaching the first packing position. Hence, the dispensing operation and subsequent packing operation can remain substantially uninterrupted and/or without delay.

In particular, the aforementioned method further includes, when the first feeder unit is empty or unable to dispense the medicaments at the first feeder position into the first collection unit, the step of:
moving said first collection unit in the collection direction and dispensing the medicaments from the second feeder unit at the second feeder position into the first collection unit.

In another embodiment, prior to positioning of the first feeder unit at the first feeder position the first feeder unit was positioned at a prior feeder position of the array of feeder positions downstream from said first feeder position, wherein the method further comprises the steps of:
removing the first feeder unit from the prior feeder position; and
moving said first feeder unit from the prior feeder position towards the first feeder position.

The 'hot standby' feeder units are placed in downstream feeder positions to allow for the aforementioned taking over of the dispensing operation of an empty feeder unit that is located in a more upstream feeder position. Over time, the feeder units that were on 'hot standby' will be emptied out themselves. Such almost empty feeder units occupy downstream feeder positions that should be occupied by full feeder units. To make space, the almost empty feeder units may be repositioned towards more upstream feeder positions so that a failure to dispense may be identified early, allowing for a new cycle of the method. The current embodiment describes the process of such repositioning for the first feeder unit, e.g. when the amount of medicaments remaining in the first feeder unit drops below a predetermined threshold.

In an embodiment thereof, the method further comprises the step of:

dispensing the medicaments from the second feeder unit at the second feeder position into the first collection unit during the moving of the first feeder unit from the prior feeder position towards the first feeder position.

The second feeder unit can therefore temporarily take over the dispensing from the first feeder unit as said first feeder unit is being repositioned. Once repositioned, the first feeder unit can resume the dispensing and the second feeder unit remains on 'hot standby' for the first feeder unit when it finally runs out of the medicaments or experiences a failure to dispense.

In another embodiment first collection unit is movable along the endless collection path over a collection range that starts at the start position and that ends at the end position The first feeder position is located in a first half of the first collection range considered from the start position. With the first feeder position located in the first half of the first collection range, there are still many downstream positions to choose from when selecting the second feeder position.

The second feeder position can be located in a second half of the collection range considered from the start position. When the first feeder unit fails to dispense the medicaments in said first half of the collection range, there is sufficient time for the dispensing device to adjust its dispensing strategy based on the second feeder unit, before reaching the second half of the collection range. While the term "half" is used here (and elsewhere in the description and claims), it does not necessarily have to be an evenly split collection range, and could instead just be in a first portion and a second portion which do not have to be equal in size.

In another embodiment, the first feeder position and the second feeder position are spaced apart in the collection direction over a spacing angle of at least five degrees, preferably at least ten degrees. When the first feeder unit fails to dispense the medicaments in said first half of the collection range, the dispensing device can adjust its dispensing strategy during the movement of the first collection unit along the spacing angle.

In another embodiment the dispensing device comprises a robotic manipulator and positioning and/or removing of the first feeder unit and the second feeder unit are performed with use of the robotic manipulator. The positioning, removing and/or repositioning of feeder units can thus be automated to quickly and/or efficiently obtain the best distribution of feeder units over the feeder positions, considering the respective amounts of medicaments remaining in said feeder units.

A second aspect provides a computer program product comprising a non-transitory computer-readable medium holding instructions that, when executed by a processor, cause a dispensing device to perform the steps of the method according to the first aspect.

The computer program product can be provided separately from the dispensing device to configure, upgrade and/or install the aforementioned functionality in said dispensing device, resulting in the previously discussed technical advantages.

A third aspect provides a dispensing device for dispensing discrete medicaments, the dispensing device comprising:

a dispensing section defining an array of feeder positions distributed along an endless collection path for holding a plurality of feeder units, the array of feeder positions comprising at least a first feeder position and a second feeder position, a collection section comprising a first collection unit that is movable with respect to the array of feeder positions in a collection direction along the endless collection path, a packaging section for packaging the medicaments received from the collection section, and a robotic manipulator and a control unit for controlling the robotic manipulator to:

position a first feeder unit at the first feeder position; and prior to removing the first feeder unit from the first feeder position, positioning a second feeder unit at the second feeder position, the second feeder position located downstream from the first feeder position in the collection direction, wherein the first feeder unit and the second feeder unit hold medicaments of the same first composition.

In one embodiment the packaging section comprises a first packaging unit at or connecting to a first packing position.

In one embodiment the first collection unit is movable between a start position downstream of a first packing position in the collection direction and an end position at or near the first packing position.

In one embodiment the first collection unit comprises a hopper.

In one embodiment the endless collection path is circular.

In one embodiment the array of feeder positions is distributed circumferentially about a rotation axis and wherein the first collection unit is rotatable about said rotation axis along the endless collection path.

Alternatively, the endless collection path is non-circular. The aforementioned dispensing device is adapted, configured and/or programmed to perform the steps of the related method and thus has the same technical advantages as the method and its respective embodiments.

A fourth aspect provides a method of continuously dispensing, collecting and packaging discrete medicaments with a dispensing device comprising a dispensing section, a collection section, and a packaging section, wherein the dispensing section comprises an array of feeder positions distributed along an endless collection path for holding a plurality of feeder units, and the collection section comprises a first collection unit that is movable with respect to the array of holding positions in a collection direction along the endless collection path to align with a plurality of the array of feeder positions, the method comprising:

placing a first feeder unit at a first feeder position in the array of feeder positions, placing a second feeder unit at a second feeder position in the array of feeder positions, the second holding position located downstream from the first holding position;

dispensing the medicaments from the first feeder unit into the first collection unit;

moving the first collection unit in the collection direction to align with the second feeder unit when the first feeder unit is empty or no longer dispenses the medicament; and dispensing the medicaments from the second feeder unit into the first collection unit, wherein the first feeder unit and the second feeder unit contain medicaments of the same first composition.

In one embodiment the steps of placing the first and second feeders are done using a robot.

One embodiment further comprises transferring the medicament from the first collection unit to a first packaging unit for packaging.

In one embodiment the method further comprises:

removing and/or replacing the first feeder unit.

A fifth aspect provides a method for dispensing discrete medicaments with a dispensing device, wherein the dispensing device comprises a dispensing section for dispensing the medicaments, wherein the dispensing section defines an array of feeder positions for holding a plurality of feeder units, wherein each feeder unit of the plurality of feeder units comprises a container for holding medicaments with a composition specific to said respective feeder unit, an outlet for dispensing the medicaments and a dispensing mechanism between the container and the outlet for controlled feeding of the medicaments from the container into the outlet, wherein the method comprises the steps of:
predicting a depletion time in the future when the medicaments in the container of a first feeder unit of the plurality of feeder units will be depleted or are past their expiry date;
providing a notification ahead of said depletion time that a second feeder unit holding medicaments with the same composition as the first feeder unit needs to presented to the dispensing device, together with a due time for presenting said second feeder unit to the dispensing device; and
continuing the dispensing of the medicaments from the first feeder unit at least until the due time.

By providing the notification, a human operator can be alerted ahead of the due time that a second feeder unit with the same medicaments is required. By providing a due time or a time window, the human operator can prioritize and/or plan ahead and prepare one or more feeder units prior to the respective due times. Meanwhile, the dispensing device may continue to dispense the remaining medicaments without interruption. When depleted or past the expiry date, the affected feeder units can be efficiently supplemented or replaced prior to, at or shortly after the due time.

Preferably, the depletion time is predicted based on a recorded amount of the medicaments in the container of the first feeder unit at a start time and a count of the medicaments dispensed from the outlet of the first feeder unit since said start time. The depletion time is thus calculated theoretically. Its accuracy is dependent on a correctness of the recorded amount at the start time and a correct count and the accuracy of the calculated average dispensing rate.

Alternatively, the depletion time is predicted based on the actual amount of medicaments remaining in the container of the first feeder unit. For example, the weight may be used as an indication of the actual amount of medicaments. Alternatively, the actual amount may be visually determined, e.g. with image recognition or one or more sensors, based on the level of the medicaments in the container.

In another embodiment the due time is equal to the depletion time. Hence, the second feeder unit may be provided just-in-time for supplementing or replacing the first feeder unit.

Alternatively, the due time is ahead of the depletion time. The remaining time before the due time and the depletion time can be used as a buffer, for example in the event that the first feeder unit is empty earlier than predicted or when the dispensing device still requires time to process the second feeder unit prior to placing it in the array of feeder positions.

In another embodiment the method further comprises the steps of:
receiving the second feeder unit at the dispensing device; and
placing the second feeder unit in one of the feeder positions of the array of feeder positions before the depletion time.

Hence, the dispensing device still has time to receive, check and/or position the second feeder unit prior to the due time. The second feeder unit can for example be positioned to be on 'hot standby', as described in the first aspect.

Preferably, the second feeder unit replaces the first feeder unit. In contrast to the first aspect, the first feeder unit and the second feeder unit may be exchanged in a single feeder position.

A sixth aspect provides a computer program product comprising a non-transitory computer-readable medium holding instructions that, when executed by a processor, cause a dispensing device to perform the steps of the method according to the fifth aspect.

The computer program product can be provided separately from the dispensing device to configure, upgrade and/or install the aforementioned functionality in said dispensing device, resulting in the previously discussed technical advantages.

A seventh aspect provides a dispensing device for dispensing discrete medicaments, wherein the dispensing device comprises a dispensing section for dispensing the medicaments, wherein the dispensing section defines an array of feeder positions for holding a plurality of feeder units, wherein each feeder unit of the plurality of feeder units comprises a container for holding medicaments with a composition specific to said respective feeder unit, an outlet for dispensing the medicaments and a dispensing mechanism between the container and the outlet for controlled feeding of the medicaments from the container into the outlet, wherein the dispensing device further comprises a graphical user interface and a control unit for controlling the graphical user interface and the plurality of feeder units, wherein the control unit comprises a processor and a non-transitory computer-readable medium holding instructions that, when executed by the processor, cause the control unit to predict a depletion time, provide a notification of said depletion time on the graphical user interface and control the plurality of feeder units to continue dispensing in accordance with the steps of the method according to the fifth aspect.

The aforementioned dispensing device is adapted, configured and/or programmed to perform the steps of the related method and thus has the same technical advantages as the method and its respective embodiments.

An eighth aspect provides a method for dispensing discrete medicaments with a dispensing device, wherein the dispensing device comprises a dispensing section for dispensing the medicaments, wherein the dispensing section defines an array of feeder positions for holding a plurality of feeder units, wherein each feeder unit of the plurality of feeder units comprises a container for holding medicaments with a composition specific to said respective feeder unit, an outlet for dispensing the medicaments and a dispensing mechanism between the container and the outlet for controlled feeding of the medicaments from the container into the outlet, wherein the method comprises the steps of:
receiving a first set of dispensing instructions requiring a first selection and a first amount of medicaments to be dispensed from the plurality of feeder units;
receiving one or more further sets of dispensing instructions to be executed after the first set of dispensing instructions, wherein at least one set of the one or more further sets of dispensing instructions requires a selection different from the first selection or an amount different from the first amount; and prior to executing the first set of dispensing instructions, determining if the plurality of feeder units contain sufficient readily available medicaments to complete the dispensing of the first selection and the first amount of medicaments in accordance with the first set of dispensing instructions;

wherein, if the plurality of feeder units or medicine transport plates contain insufficient readily available medicaments to complete the dispensing of the first selection and the first amount of medicaments in accordance with the first set of dispensing instructions, the method further comprises the step of:

executing one or more sets of the one or more further sets of dispensing instructions prior to executing said first set of dispensing instructions.

The one or more sets of dispensing instructions can be prioritized over the first set of dispensing instructions to allow for supplementing of the missing amount of medicaments. The dispensing of the first selection and the first amount of medicaments can be commenced as soon as possible after the prioritized sets of dispensing instructions have been completed. Changing the order of the sets of instructions can thus prevent at least a part of the downtime that would be caused when the dispensing device would have processed the sets of instructions in their original order.

Preferably, an action is taken during the executing of the one or more sets of the one more further sets of dispensing instructions to ensure that the plurality of feeder units contain sufficient readily available medicaments to complete the dispensing of the first selection and the first amount of medicaments in accordance with the first set of dispensing instructions. By taking the appropriate action during the execution of the one or more further sets of dispensing instructions, at least some of the time required to take the appropriate action can be used to continue the dispensing operation. More preferably, the action is to present one or more feeder units to the dispensing device for supplementing or replacing one or more feeder units of the plurality of feeder units that contain insufficient readily available medicaments to complete the dispensing of the first selection and the first amount of medicaments in accordance with the first set of dispensing instructions. One or more feeder units may for example be placed on 'hot standby' for feeder units that are almost empty, in accordance with the first aspect, so that the dispensing can be resumed without interruption.

In another embodiment the first set of dispensing instructions and the one or more further sets of dispensing instructions share a logistical parameter that link the first set of dispensing instructions and the one or more further sets of dispensing instructions to a common batch. Preferably, the logistical parameter is a delivery address. By keeping the sets of dispensing instructions of a common batch together, changing the order in which the sets of dispensing instructions are processed has less impact on the further logistics of said common batch. For example, it does not matter if the order of the sets of dispensing instructions is changed if the medicaments that are dispensed as a results of said dispensing instruction all have to be delivered to the same delivery address.

A ninth aspect provides a computer program product comprising a non-transitory computer-readable medium holding instructions that, when executed by a processor, cause a dispensing device to perform the steps of the method according to the eighth aspect.

The computer program product can be provided separately from the dispensing device to configure, upgrade and/or install the aforementioned functionality in said dispensing device, resulting in the previously discussed technical advantages.

A tenth aspect provides a dispensing device for dispensing discrete medicaments, wherein the dispensing device comprises a dispensing section for dispensing the medicaments, wherein the dispensing section defines an array of feeder positions for holding a plurality of feeder units, wherein each feeder unit of the plurality of feeder units comprises a container for holding medicaments with a composition specific to said respective feeder unit, an outlet for dispensing the medicaments and a dispensing mechanism between the container and the outlet for controlled feeding of the medicaments from the container into the outlet, wherein the dispensing device further comprises a control unit, wherein the control unit comprises a processor and a non-transitory computer-readable medium holding instructions that, when executed by the processor, cause the control unit to execute the steps of the method according to the eighth aspect.

The aforementioned dispensing device is adapted, configured and/or programmed to perform the steps of the related method and thus has the same technical advantages as the method and its respective embodiments.

An eleventh aspect provides a method for dispensing discrete medicaments with a first feeder unit, wherein the first feeder unit comprises a container for holding medicaments of a first composition, an outlet for dispensing the medicaments and a dispensing mechanism between the container and the outlet for controlled feeding of the medicaments from the container into the outlet, wherein the method comprises the steps of:

determining a remaining value indicative of the amount of the medicaments remaining in the container;

comparing said remaining value to a threshold value;

making a selection between a complete empty detection mode when said remaining value is above the threshold value and a shortened empty detection mode when the remaining value is below the threshold value;

executing the selected one of the complete empty detection mode and the shortened empty detection mode when no medicament is fed from the container towards the outlet after controlling the dispensing mechanism.

The method above is based on the assumption that if the first feeder unit is expected to be almost empty, it is not necessary to do elaborate checks on the emptiness of said first feeder unit. If there are any medicaments remaining, the remaining amount will be very little and the risk of unnecessarily removing the first feeder unit is relatively small. Hence, only a limited number of attempts or a limited number of actions is performed to check that the first feeder unit is empty. In contrast, when the remaining amount is still above the threshold value, it assumed that there are sufficient readily available medicaments remaining to successfully dispense and that there is a different reason for any failure to dispense. In other words, by making a selection between the two modes, a reliable empty detection for both an almost empty first feeder unit and a relatively full first feeder unit. The shortened empty detection mode can save considerable time, e.g. in the range of ten to twenty seconds, compared to the complete empty detection mode. Hence, downtime of the dispensing device as a result of empty detection checks can be reduced considerably.

Preferably, the complete empty detection mode comprises the step of performing a first action a first number of instances, wherein the shortened empty detection mode comprises the step of performing the first action for a second number of instances less than the first number of instances. Reducing the number of instances of the first action can considerably save time of the empty detection check between the modes.

More preferably, the first action is controlling the dispensing mechanism. The controlling of the dispensing mechanism should result in a dispense of the solid substance. Repeatedly attempts at controlling the dispensing mechanism, e.g. by moving it in multiple steps, could allow medicaments to stabilize and find their way into the dispensing mechanism.

Alternatively, the complete empty detection mode comprises the steps of performing a first action and a second action different from the first action, wherein the shortened empty detection mode comprises only one of the first action and the second action. The second action may trigger a different dispensing result than the first action. The second action may for example be shaking of the first feeder unit, e.g. with a robotic manipulator. The first or the second action may be left out of the shortened empty detection mode to save time between the modes.

In a further embodiment the complete empty detection mode has a first duration, wherein the shortened empty detection mode has a second duration shorter than the first duration. As already mentioned, the shortened empty detection mode may involve less actions or less types of actions, thus resulting in a shorter timespan for completing the empty detection in said mode. Alternatively, the shortened empty detection mode may be limited in time, or the actions may be performed quicker to save time.

In a further embodiment the remaining value is predicted based on a recorded amount of the medicaments in the container of the first feeder unit at a start time and a count of the medicaments dispensed from the outlet of the first feeder unit since said start time. The depletion time is thus calculated theoretically. Its accuracy is dependent on a correctness of the recorded amount at the start time and a correct count.

Alternatively, the remaining value is determined based on the actual amount of medicaments remaining in the container of the first feeder unit. For example, the weight may be used as an indication of the actual amount of medicaments. Alternatively, the actual amount may be visually determined, e.g. with image recognition or one or more sensors, based on the level of the medicaments in the container.

A twelfth aspect provides a computer program product comprising a non-transitory computer-readable medium holding instructions that, when executed by a processor, cause a dispensing device with a first feeder unit to perform the steps of the method according to the eleventh aspect.

The computer program product can be provided separately from the dispensing device to configure, upgrade and/or install the aforementioned functionality in said dispensing device, resulting in the previously discussed technical advantages.

A thirteenth aspect provides a dispensing device for dispensing discrete medicaments, wherein the dispensing device is provided with a first feeder unit that comprises a container for holding medicaments of a first composition, an outlet for dispensing the medicaments and a dispensing mechanism between the container and the outlet for controlled feeding of the medicaments from the container into the outlet, wherein the dispensing device further comprises a control unit, wherein the control unit comprises a processor and a non-transitory computer-readable medium holding instructions that, when executed by the processor, cause the control unit to execute the steps of the method according to the eleventh aspect.

The aforementioned dispensing device is adapted, configured and/or programmed to perform the steps of the related method and thus has the same technical advantages as the method and its respective embodiments.

The various aspects and features described and shown in the specification can be applied, individually, wherever possible. These individual aspects, in particular the aspects and features described in the attached dependent claims, can be made subject of divisional patent applications.

BRIEF DESCRIPTION OF THE DRAWINGS

The invention will be elucidated on the basis of an embodiment shown in the attached schematic drawings, in which:

FIG. 2A show a top view of the dispensing device according to FIG. 1;

FIG. 2B shows a front view of a first feeder unit at a prior feeder position of the dispensing section, as indicated by the arrow connecting FIG. 2B with FIG. 2A;

FIG. 2C shows a front view of a second feeder unit at a loading drawer position of the dispensing section, as indicated by the arrow connecting FIG. 2C with FIG. 2A;

FIGS. 3A, 3B and 3C show views corresponding to FIGS. 2A, 2B and 2C, respectively, with the second feeder unit being moved from the loading drawer position to a second feeder position of the dispensing section;

FIGS. 4A, 4B and 4C show views corresponding to FIGS. 3A, 3B and 3C, respectively, with the first feeder unit being moved from the prior feeder position to a first feeder position of the dispensing section;

FIGS. 5A, 5B and 5C show views corresponding to FIGS. 4A, 4B and 4C, respectively, in which the first feeder unit has been removed from the dispensing device;

FIG. 9A shows a top view of an alternative dispensing device with a dispensing section, a collection section and a packaging section according to a second embodiment FIG. 9B shows a front view of a first feeder unit at a prior feeder position of the dispensing section, as indicated by the arrow connecting FIG. 9B with FIG. 9A; and FIG. 9C shows a front view of a second feeder unit at a loading drawer position of the dispensing section, as indicated by the arrow connecting FIG. 9C with FIG. 9A.

DETAILED DESCRIPTION OF THE INVENTION

Figure 1:
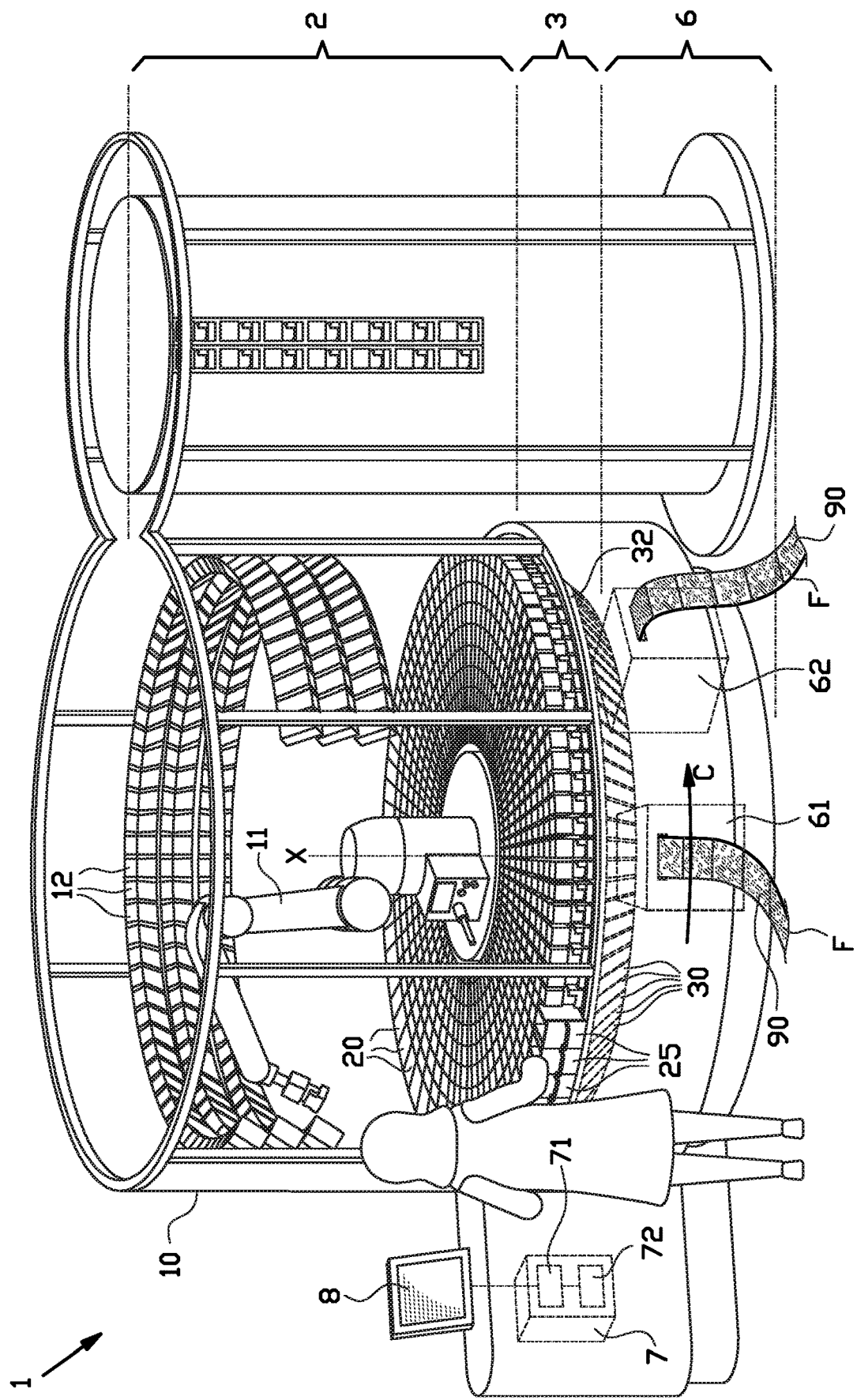
FIG. 1 shows an isometric view of the dispensing device with a dispensing section, a collection section and a packaging section according to a first embodiment.

FIG. 1 shows a dispensing device 1 according to a first embodiment for dispensing discrete medicaments, discrete solid medicaments, pharmaceuticals or solid items, articles or substances 90 for medical use, e.g. pills, tablets, capsules or the like. The medicaments are 'discrete' in the sense that they can be dispensed one-by-one, individually, separately or in dose units.

The dispensing device 1 comprises a dispensing section 2 for dispensing the medicaments 90, a collection section 3 for collecting the medicaments 90 from the dispensing section 2 and a packaging section 6 for packing the medicaments 90. The collection section 3 is located below or vertically below the dispensing section 2. The packaging section 6 is located below or vertically below the collection section 3. The dispensing device 1 further comprises a housing 10 for shielding the aforementioned sections 2, 3, 6 from unauthorized access.

The dispensing section 2 defines an array of feeder positions 20 for receiving or holding a plurality of canisters, tablet cases or feeder units 40. Each feeder position comprises a docking member for mating with or receiving a respective one of the feeder units 40, with an appropriate aperture or channel to allow passage of dispensed medicaments 90 through the feeder position 20 into the collection section 3 underneath. The array of feeder positions 20 is distributed along an endless collection path Z1. In this example, the endless collection path Z1 is circular or substantially circular and the array of feeder positions 20 is distributed circumferentially about a rotation axis X. More in particular, the array of feeder positions 20 is distributed circumferentially or according to a radial grid, e.g. in a plurality of radially extending rows arranged side-by-side or adjacent in a circumferential direction about the rotation axis X. Preferably, the housing 10 extends cylindrically around the array of feeder positions 20. In this example, the circumferential walls of the housing 10 are provided with a plurality of stock positions 12 for holding temporarily unused or auxiliary feeder units 40.

The dispensing device 1 is further provided with a robotic manipulator 11, e.g. which can include a robot arm, for automatic, automated or autonomous handling, positioning, removing and/or repositioning the feeder units 40 with respect to the array of feeder positions 20. The robotic manipulator 11 is provided with a gripper head to pick-and-place the feeder units 40. In this embodiment, the robotic manipulator 11 is located at the center of the array of feeder positions 20, e.g.close to, at or near the rotation axis X. In said position, all feeder positions 20 and stock positions 10 are conveniently within reach of the robotic manipulator 11.

FIG. 2B show a feeder unit 40 of the plurality of feeder units 40 in more detail. The description of the feeder unit 40 hereafter is representative for all feeder units 40 of the plurality of feeder units 40.

As shown in FIG. 2B, each feeder unit 40 comprises a container 50 for holding an amount of the medicaments 90 with a composition 91 specific to said respective feeder unit 40. The term 'composition' is to be interpreted as the chemical or pharmaceutical composition of the medicament 90, e.g. the combination of active ingredients, that could include slight variations. Each feeder unit 40 typically only holds a medicaments 90 of a single composition. The container 50 has a volume that may hold several hundreds or more (or less) of the medicaments 90, depending on their size and shape.

Each feeder unit 40 further comprises an outlet 51, e.g. a fall pipe, for dispensing the medicaments 90 towards the collection section 3 and a dispensing mechanism 52 between the container 50 and the outlet 51 for controlled feeding of the medicaments 90 from the container 50 into the outlet 51. In this embodiment, the dispensing mechanism 52 comprises a wheel that acts as a revolving door to singulate and feed the medicaments 90 one by one towards the outlet 51. It will be apparent to one skilled in the art that alternative dispensing mechanisms may be provided which can singulate the medicaments 90.

Each feeder unit 40 may further be provided with one or more sensors 53, 54, e.g. a vision camera, a photosensor, a laser sensor, a level sensor, a weight sensor or the like, for verifying the type, composition and/or integrity of the medicaments 90, and for counting the amount of medicaments 90 that have been dispensed.

As best seen in FIG. 1, the dispensing section 2 further comprises a feeder loading member 24 with a plurality of feeder loading positions 25 for receiving new feeder units 40 into the dispensing device 1 and/or for removing feeder units 40 from the dispensing device 1. In this example, the feeder loading member 24 is formed as a drawer. Alternatively, a door or the like may be used. The dispensing section 2 may optionally comprise a manual loading position 26 for receiving a manual loading member (not shown), e.g. a medicine transport plate, that is manually loaded with medicaments 90 which are unsuitable to be dispensed automatically with the aforementioned feeder units 40.

As further shown in FIG. 1, the collection section 3 comprises a plurality of collection units, in particular collection hoppers 30, which are open at a side facing the dispensing section 2 to receive selectively dispensed medicaments 90 from one or more of the feeder units 40. In this example, each collection hopper 30 extends underneath a plurality of feeder units 40 at the same time to receive the medicaments 90 from any of those feeder units 40. Each collection hopper 30 tapers towards the bottom and is provided, at said bottom, with a valve (not shown) that can be operated to drop the collected medicaments 90 into the packaging section 6.

In this embodiment, the plurality of collection hoppers 30 are distributed circumferentially about the rotation axis X. More in particular, the plurality of collection hoppers 30 are held in a collection frame 32 that is movable along the endless collection path Z1, e.g. by rotating about said rotation axis X to move the plurality of collection hoppers 30 relative to the array of feeder positions 20 in the dispensing section 2. The rotation may be a stepped rotation, wherein each step aligns the plurality of collection hoppers 30 with a next group of feeder units 40 in the array of feeder positions 20. Each collection hopper 30 extends radially along a row of radially arranged feeder positions 20.

In normal operation, the collection frame 32 is rotated one-way in a collection direction C along the endless collection path Z1 so that each collection hopper 30 can make a full revolution of three-hundred-and-sixty degrees, about the rotation axis X and visit all feeder positions 20 of the array of feeder positions 20, though in some embodiments the rotational movement could be more limited.

The packaging section 6 comprises a first packaging unit 61 at a first packing position or a first angular packing position P1 about the rotation axis X. Optionally, the packaging section 6 may comprise a second packaging unit 62 at a second packing position or a second angular packing position P2 to increase the packing efficiency of the dispensing device 1. The valves of the collection hoppers 30 are operated when a respective one of the collection hoppers 30 is in a position overhead or directly above a selected one of the packaging units 61, 62 to drop the collected medicaments 90 into the respective packaging unit 61, 62. Each packaging unit 61, 62 comprises a stock member for holding the packaging material, in this example a foil, a printer for printing information about the medicaments 90 on the foil, a filling member for positioning the foil to receive the medicaments 90, a seal member for forming a pouch around the received medicaments 90, a perforation member for providing the foil with perforations between subsequently formed pouches and an output member for outputting the packaged medicaments F from the dispensing device 1.

Alternatively, one of the packaging units 61, 62 or both may be arranged for packaging the medicaments 90 in a storage material other than a foil, e.g. in vials, bottles or cards.

The first packing position P1 and/or the second packing position P2 can be fixed relative to the rotation axis X, at least during the dispensing operation.

As shown in FIG. 1, the dispensing device 1 is further provided with a control unit 7 that is operationally and/or electronically connected with the robotic manipulator 11, the feeder units 40, the packaging units 61, 62 and other electronic equipment such as drives, sensors and the like, to control the operation of the dispensing device 1. The control unit 7 comprises a special purpose processor 71 and a computer-readable medium 72 holding computer-readable code or instructions that, when executed by the processor 71, cause the dispensing device 1 to operate according to the methods described in more detail hereafter. The computer-readable medium 72 is non-transitory or tangible, e.g. a physical data carrier such as a hard-drive, a USB-drive, a RAM memory or the like.

The dispensing device 1 may further be provided with a graphical user interface 8, for example a screen, to provide a human operator with useful information about the dispensing, collection and packing operation.

Methods of operating the dispensing device 1 will be described hereafter with reference to a first feeder unit 41 and a second feeder unit 42 of the plurality of feeder units 40, a first collection hopper 31 of the plurality of collection hoppers 30 and the first packaging unit 61 of the two packaging units 61, 62 only. It will however be clear to one skilled in the art that the dispensing device 1 can be operated in substantially the same way for any other selection of the feeder units 40, the collection hoppers 30 and/or the packaging units 61, 62 to ensure a flexible and substantially uninterrupted or continuous dispensing, collection and packing process.

As shown in FIGS. 2A, the first collection hopper 31 is rotatable with respect to the array of feeder positions 20 in a collection direction C about the rotation axis X between a start position or an angular start position A downstream from the first packing position P1 in the collection direction C and an end position or an angular end position B at or near, in this case, above the first packing position P1. In other words, the first collection hopper 31 is rotatable about the rotation axis X over a collection range R that starts at the angular start position A and that ends at the angular end position B. In this example, the collection range R is five degrees short of three-hundred-and-sixty degrees, almost a full revolution.

When the control unit 7 receives a set of instructions for dispensing a selection and amount of the medicaments 90 from the feeder units 40, the control unit 7 determines which feeder units 40 to use, based on the current or remaining amount of medicaments 90 in said feeder units 40. The control unit 7 may be configured to store on the computer-readable medium 72 the amount of medicaments 90 in the feeder units 40 at a start time, and monitor the dispensing of said medicaments 90, e.g. with the use of a sensor 54 for counting, to calculate or predict the remaining amount of medicaments 90 in each feeder unit 40. When one of the feeder units 40 is close to being empty, the control unit 7 can be configured to control the robotic manipulator 11 to already position another feeder unit 40 with the same medicaments 90, medicaments 90 of the same type, the same brand, the same producer and/or the same composition 91 as the feeder unit 40 that is close to being empty on 'hot standby' to take over the dispensing from the feeder unit 40 that is getting empty as soon as it is actually empty. In other words, the medicaments 90 in the aforementioned pair of feeder units 40 has the same active ingredient(s) and/or is pharmaceutically similar or identical. The other feeder unit 40 may come from one of the stock positions 12 within the dispensing section 2. Alternatively, the control unit 7 may notify the human operator to present a new feeder unit 40 to the dispensing device 1 at the feeder loading member 24.

While the first and second feeder units 41, 42 would typically have the same type of medicaments 90, in some embodiments, the medicaments 90 may not be exactly identical but could act as replacements for each other, e.g., when no identical medicament 90 is available, however typically only upon approval by the human operator.

FIGS. 2A-2C, 3A-3C, 4A-4C and 5A-5C show the process of the first feeder unit 41 becoming empty and positioning a second feeder unit 42 on 'hot standby', in accordance with the present invention.

In particular, FIG. 2A shows the situation in which the first feeder unit 41, as shown in FIG. 2B, is in a prior feeder position 23 of the array feeder positions 20. As shown in FIG. 2B, the first feeder unit 41 is actively dispensing. The prior feeder position 23 is 'prior' in the sense that the first feeder unit 41 was positioned there during a previous cycle of the method, when it was still full or relatively full with medicaments 90 of a first composition 91. Now, the first feeder unit 41 is becoming empty, for example there is less than fifty percent of the original amount left, and in some embodiments less than thirty percent of the original amount. In this example, the prior feeder position 23 is in the second half of the collection range R, considered in collection direction C from the start position A. The method according to the present invention is aimed at placing feeder units 40 that are become empty upstream in the collection range R relative to the collection direction C, e.g. in the first half of said collection range R, considered in the collection direction C from the start position A. As shown in FIG. 4A, the first feeder unit 41 is moved towards a first feeder position 21 of the array of feeder positions 20 in the first half of the collection range R, upstream of the prior feeder position 23 of FIG. 2A.

Before moving the first feeder unit 41 from the prior feeder position 23 towards the first feeder position 21, the second feeder unit 42 can already be present in the dispensing device 1 at one of the feeder loading positions 25 in the feeder loading member 24, ready for insertion into the dispensing device 1 and pick-up by the robotic manipulator 11, as shown in FIG. 2A. Alternatively, the second feeder unit 42 may be one of the feeder units 40 that is already in the collection section 2, e.g. in one of the stock positions 12, as shown in FIG. 1. The second feeder unit 42 is typically filled with medicaments 90 of the same first composition 91 as the first feeder unit 41.

FIG. 3A shows the second feeder unit 42 after it has been picked up by the robotic manipulator 11 from the feeder loading position 25 and positioned in the feeder position 22 of the array of feeder positions 20. In this example, the second feeder position 22 is downstream from the prior feeder position 23 in the collection direction C, although —at this stage —this is not strictly necessary. Alternatively, the prior feeder position 23 may be downstream from the second feeder position 22 in the collection direction C. As shown in FIG. 3C, the second feeder unit 42 can temporarily take over dispensing from the first feeder unit 41, if needed, during the relocation of said first feeder unit 41 between FIGS. 2A and 4A, to ensure continuity of the dispensing of the medicaments 90 of the first composition 91.

FIG. 4A shows the situation in which the first feeder unit 41 has been removed from the prior feeder position 23 by the robotic manipulator 11 and has been positioned in the first feeder position 21. The first feeder unit 41 can now resume dispensing, as shown in FIG. 4B, until the medicaments 90 of the first composition 91 run out or the first feeder unit 41 is no longer able to dispense the remaining medicaments 90. The second feeder unit 42, as shown in FIG. 4C, is now on 'hot standby' to take over dispensing from the first feeder unit 41 if the first feeder unit 41 fails to dispense the medicaments 90.

FIG. 5A shows the situation in which the first feeder unit 41, as shown in FIG. 5B, is empty or has failed to dispense the medicaments 90. Consequently, the first collection hopper 31 has failed to collect the required medicaments 90 of the first composition 91 from the first feeder unit 41. The first collection hopper 31 does not have to wait for the first feeder unit 41 to be replaced. Instead, the first collection hopper 31 can be moved or rotated further in the collection direction C along the endless collection path Z1 until it is underneath or directly underneath the second feeder unit 42 in the second feeder position 22. In the meantime, the controller 7 has adapted its dispensing strategy taking into account the failure to dispense the medicaments 90 of the first composition 91 from the first feeder unit 41 and assigns the second feeder unit 42, as shown in FIG. 5C, to take over the dispensing from said first feeder unit 41. In other words, the second feeder unit 42 can dispense the missing medicaments 90 of the first composition 91.

The first feeder position 21 and the second feeder position 22 are typically spaced apart in the collection direction over a spacing angle H of at least five degrees, preferably at least ten degrees or at least one radial row of the array of feeder positions 20, to allow for sufficient time for the control unit 7 and/or the human operator to adjust the dispensing strategy, e.g. within the normal time it would take the first collection hopper 31 to travel, without interruption, from the first feeder position 21 to the second feeder position 22.

The empty first feeder unit 41 can be picked up by the robotic manipulator 11 and moved to one of the feeder loading positions 25 at the feeder loading member 24 to remove or unload said empty first feeder unit 41 from the dispensing device 1.

Figure 6:
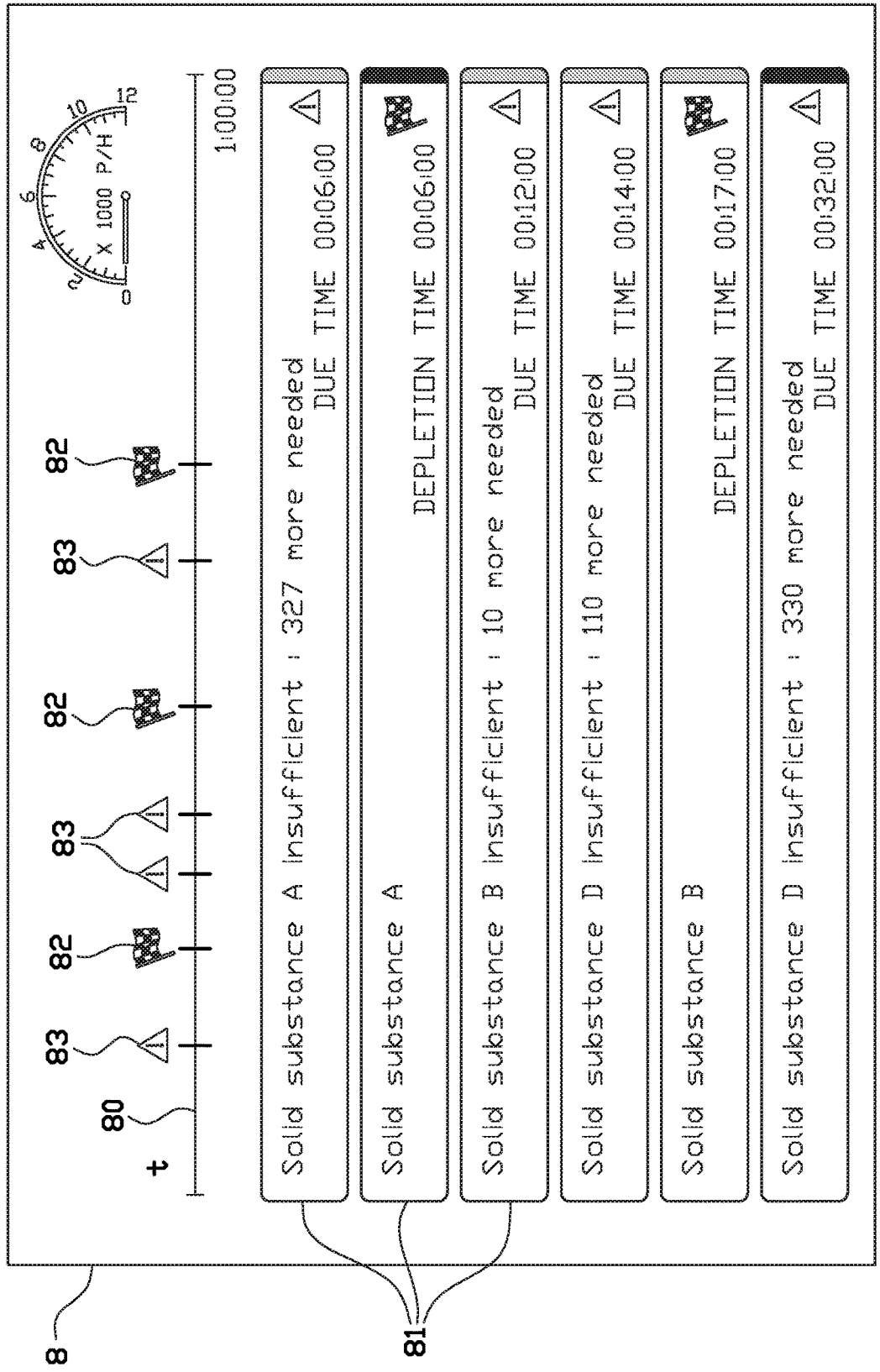
FIG. 6 shows a screen of a graphical user interface providing a timeline for replacing or supplementing feeder units in the dispensing section of the dispensing device according to FIG. 1.

FIG. 6 shows the graphical user interface 8 of the aforementioned dispensing device 1 in more detail. The graphical user interface 8 is generated by the control unit 7 as shown in FIG. 1. As shown in FIG. 6, the graphical user interface 8 presents the human operator with an optional timeline 80 and one or more notifications 81 regarding depletion times 82 of one or more feeder units 40. The notifications 81 may be provided on the timeline 80 and/or separately from said timeline 80. The timeline 80 has a time axis t from left (current time) to right (future). The depletion times 82 are predicted or calculated by the control unit 7. The depletion times 82 may be predicted or calculated based on recorded amounts of the medicaments 90 in the containers 50 of the respective feeder units 40 at a start time and a count of the medicaments 90 dispensed from the outlets 51 of the respective feeder units 40 since said start time, e.g. based on the count sensor 54 shown in FIG. 2B. Alternatively, the depletion time 82 can be predicted based on sensor data from the sensors 53, 54, as shown in FIG. 2B, indicative of the actual amount of medicaments 90 remaining in the containers 50 of the respective feeder units 40, e.g. based on data from a vision camera, level sensors and/or a weight sensor.

Each notification 81 is provided ahead of the predicted depletion time 82 together with a due time 83 for supplementing the medicaments 90 that will be missing at the respective depletion time 82. The notification 81 may simply indicate how much more of the medicaments 90 of a specific composition 91 are required, or it may indicate or request a specific feeder unit 40 holding medicaments 90 of the same composition 91 to replace or supplement the feeder unit 40 that is almost empty. The human operator can retrieve the required feeder unit 40 and present it to the dispensing device 1 in the manner as described before.

In the meantime, the dispensing of the medicaments 90 from the one or more affected feeder units 40 is continued at least until the due time 83. Hence, the dispensing operation can remain uninterrupted.

The due time 83 is preferably chosen to be ahead of the depletion time 82 with some safety margin, e.g. at least one minute, at least three minutes or at least five minutes, to allow the human operator to retrieve and/or prepare the required feeder unit 40. The human operator may also combine retrieving one or more required feeder units 40 at the same time. Alternatively, the due time 83 may be set to be equal to the depletion time 82, thus requiring a more timely or strict approach by the human operator.

The one or more required feeder units 40 can be picked-up and placed by the robotic manipulator 11 in respective feeder positions 20 before the respective depletion times 82, thus preventing downtime of the dispensing device 1. The process may for example be similar to the method described earlier in relation to the first feeder unit 41 and the second feeder unit 42. Alternatively, the second feeder unit 42 may replace the first feeder unit 41 in a single feeder position 20 as soon as the first feeder unit 41 has been depleted or the medicaments 90 contained therein are past their expiry date.

Figure 7A:
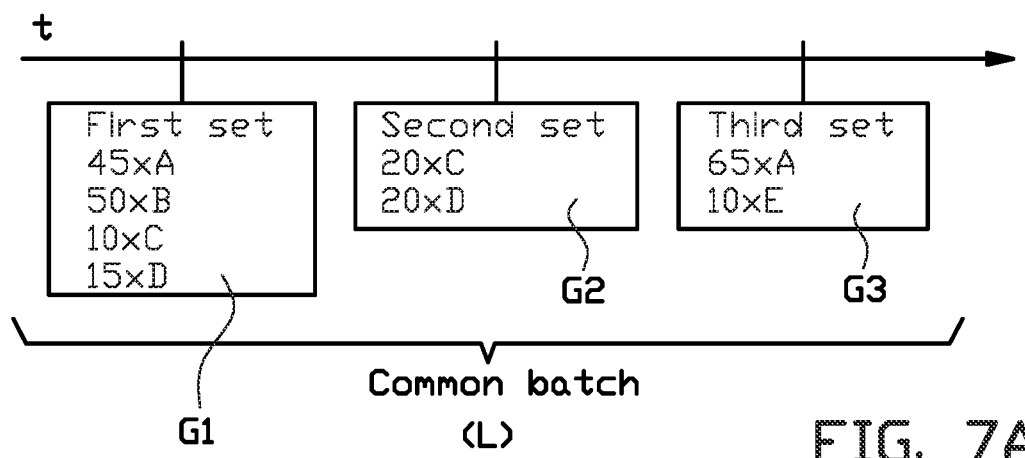
FIG. 7A shows a schematically shows a common batch with three sets of dispensing instructions for dispensing different selections and amounts of medicaments in the dispensing device according to FIG. 1.
Figure 7C:
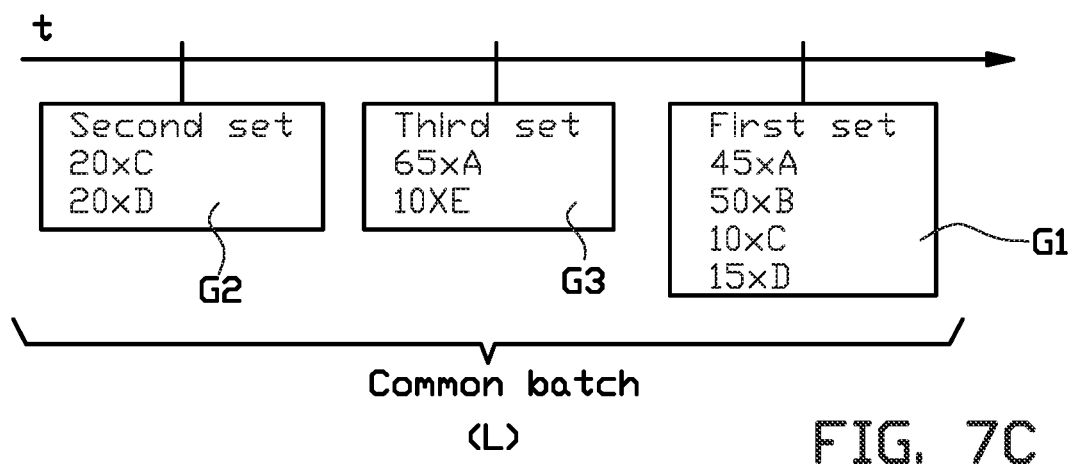
FIG. 7C schematically shows the common batch of FIG. 7A after reordering the three sets of dispensing instructions as a result of the prioritization in the method according to FIG. 7B.
Figure 7B:
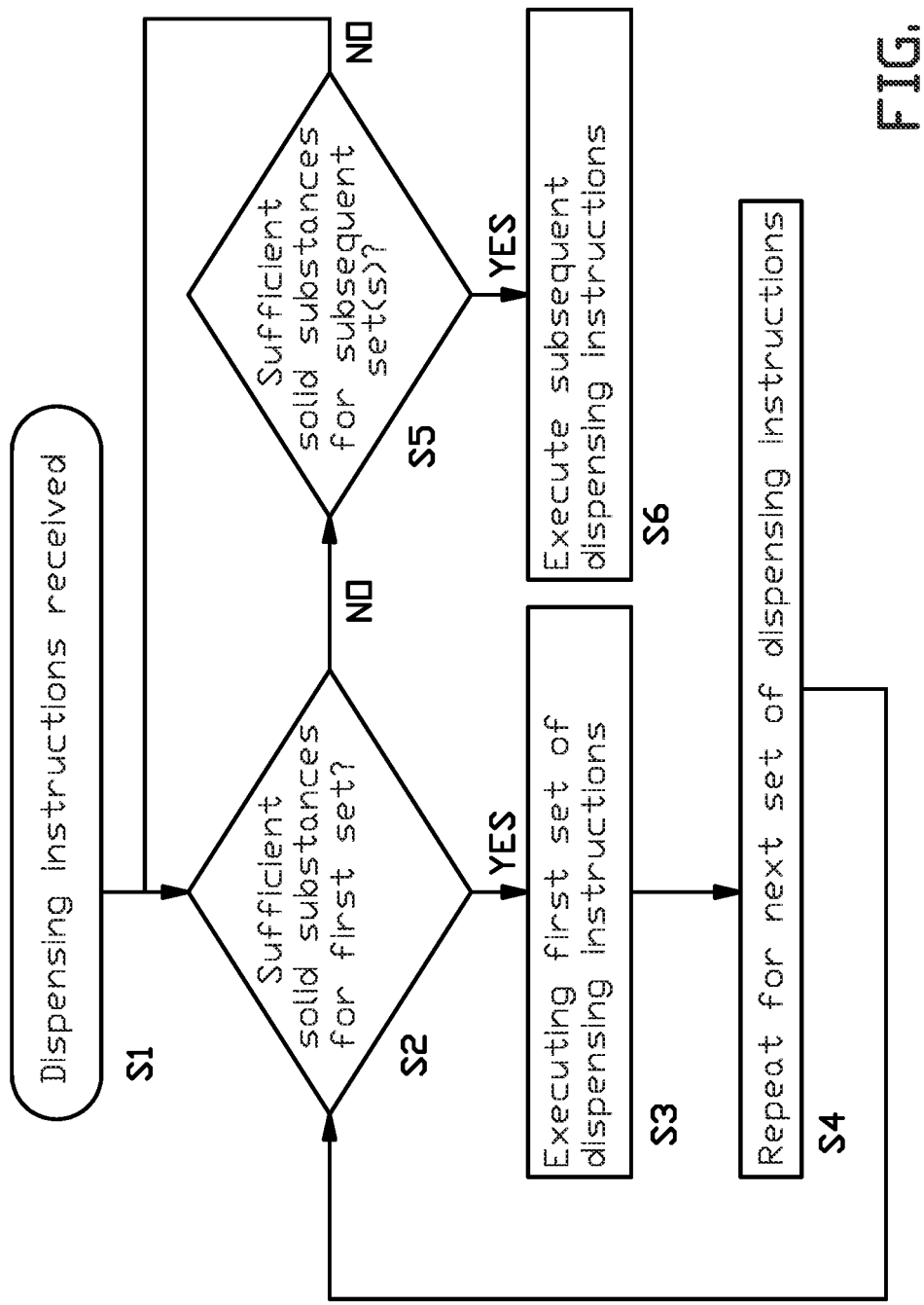
FIG. 7B shows a diagram of the steps of a method for prioritizing one or more of the sets of dispensing instructions according to FIG. 7A for execution by the dispensing device.

FIGS. 7A, 7B and 7C are related to a method for dispensing the medicaments 90 with the use of the aforementioned dispensing device 1, including steps for changing the order in which a sets of dispensing instructions G1, G2, G3 are executed by the processor 71 of the control unit 7, as shown in FIG. 1.

In particular, FIG. 7A shows a first set of dispensing instructions G1 requiring forty-five times a medicament 90 of a composition A, fifty times a medicament 90 of composition B, ten times a medicament 90 of composition C and fifteen times a medicament 90 of composition D. Similarly, a second set of dispensing instructions G2 and a third set of dispensing instructions G3 are provided which require a different amount of medicaments 90 of similar compositions C, D or different compositions E, F. It is originally intended that the processor 71 executes the sets of dispensing instructions G1, G2, G3 in the order as shown, from left (current time) to right (future) along a time axis t.

FIG. 7B shows a diagram of the steps of a method, to be performed by the processor 71, for determining an alternative order for executing the sets of dispensing instructions G1, G2, G3 when the first set of dispensing instructions G1 cannot be completed with the medicaments 90 remaining in the plurality of feeder units 40.

In particular, the method comprises the steps of receiving the sets of dispensing instructions G1, G2, G3 (step S1) and prior to executing the first set of dispensing instructions G1, having the control unit 7 determine if the plurality of feeder units 40 contain sufficient readily available medicaments 90 to complete the dispensing of the first selection and the first amount of medicaments 90 in accordance with the first set of dispensing instructions G1 (step S2). The medicaments 90 are 'readily available' if there sufficient medicaments 90 left in the plurality of feeder units 40 which are cleared to be dispensed. Said clearance may be revoked when the medicaments 90, at the time of dispensing, would be beyond the expiry date registered in the system. In the affirmative, the control unit 7 may proceed to execute the first set of dispensing instructions (step S3) and repeat the determination for each subsequent set of dispensing instructions (step S4).

However, if the plurality of feeder units 40 contain insufficient readily available medicaments 90 to complete the dispensing of the first selection and the first amount of medicaments 90 in accordance with the first set of dispensing instructions G1, the control unit 7 switches to executing one or more sets of the one or more further sets of dispensing instructions G2, G3 (step S6), optionally preceded by a determination if the feeder units 40 contain sufficient readily available medicaments 90 to complete the dispensing of the selection and amount of medicaments 90 associated with each subsequent further set of dispensing instructions G2, G3 (step S5). Hence, the order in which the sets of dispensing instructions G1, G2, G3 are executed can be changed, as shown in FIG. 7C.

During the executing of the one or more further sets of dispensing instructions G2, G3, an action can be taken to ensure that the plurality of feeder units 40 contain sufficient readily available medicaments 90 to complete the dispensing of the first selection and the first amount of medicaments 90 in accordance with the first set of dispensing instructions G1. In particular, a human operator may be notified to replace or supplement the affected feeder units 40, for example in accordance with the method as shown in FIGS. 2A-2C, 3A-3C, 4A-4C and 5A-5C.

In the event that there are insufficient readily available medicaments 90 to complete dispensing according to any one of the sets of dispensing instructions G1, G2, G3, the control unit 7 will return to the determination of step S2 and wait for the medicaments 90 to be supplemented.

As shown in FIGS. 7A and 7C, the first set of dispensing instructions G1 and the one or more further sets of dispensing instructions G2, G3 preferably share a logistical parameter L that link the first set of dispensing instructions G1 and the one or more further sets of dispensing instructions G2, G3 to a common batch. The control unit 7 is restricted to changing the order of the sets of dispensing instructions G1-G3 within the common batch only. The logistical parameter L may be a delivery address, a patient order, a client name or the like.

Figure 8A:
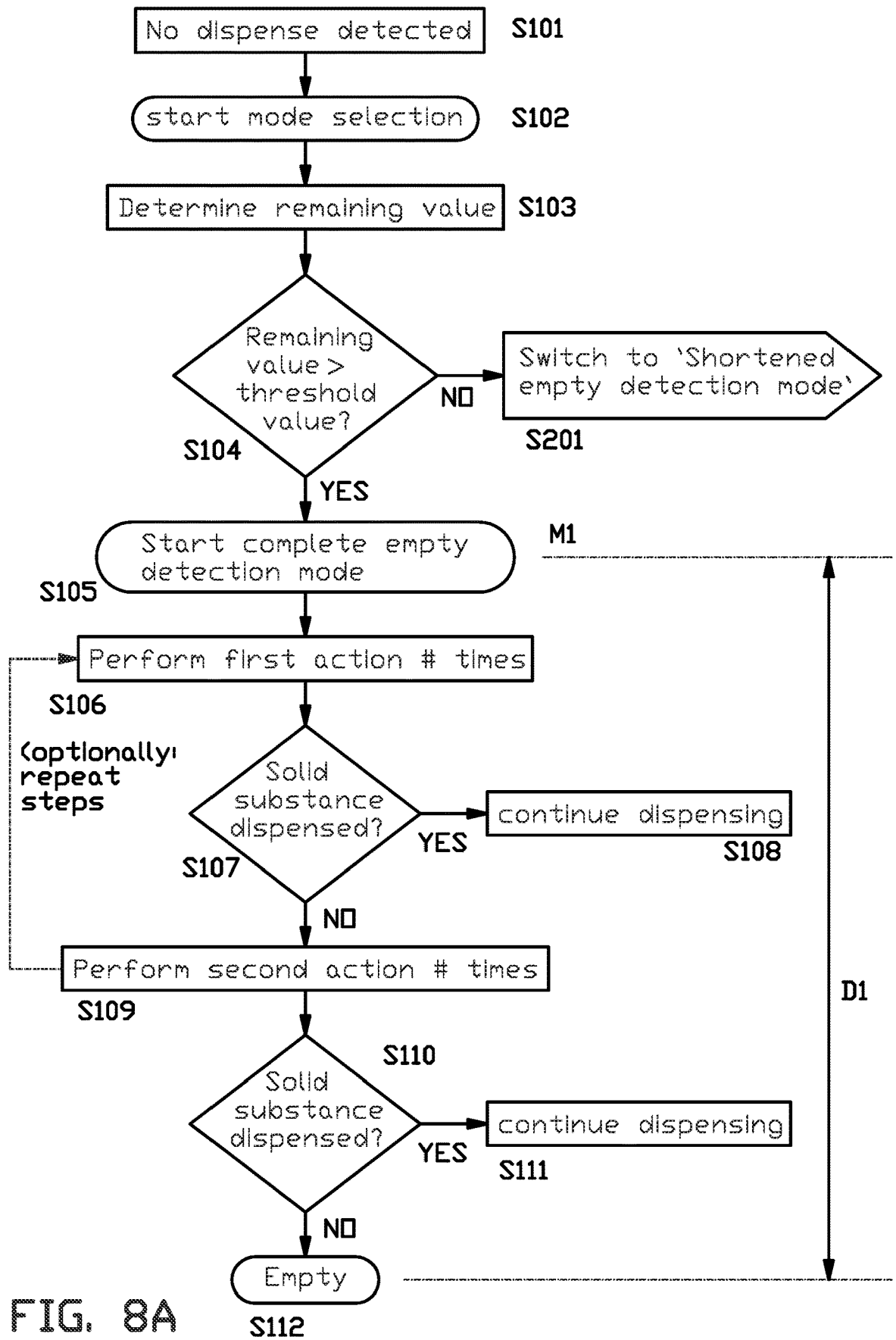
FIGS. 8A and 8B show two parts of a diagram of the steps of a method for selecting between a complete empty detection mode and a shortened empty detection mode, to detect if the feeder units in the dispensing device according to FIG. 1 are empty.
Figure 8B:
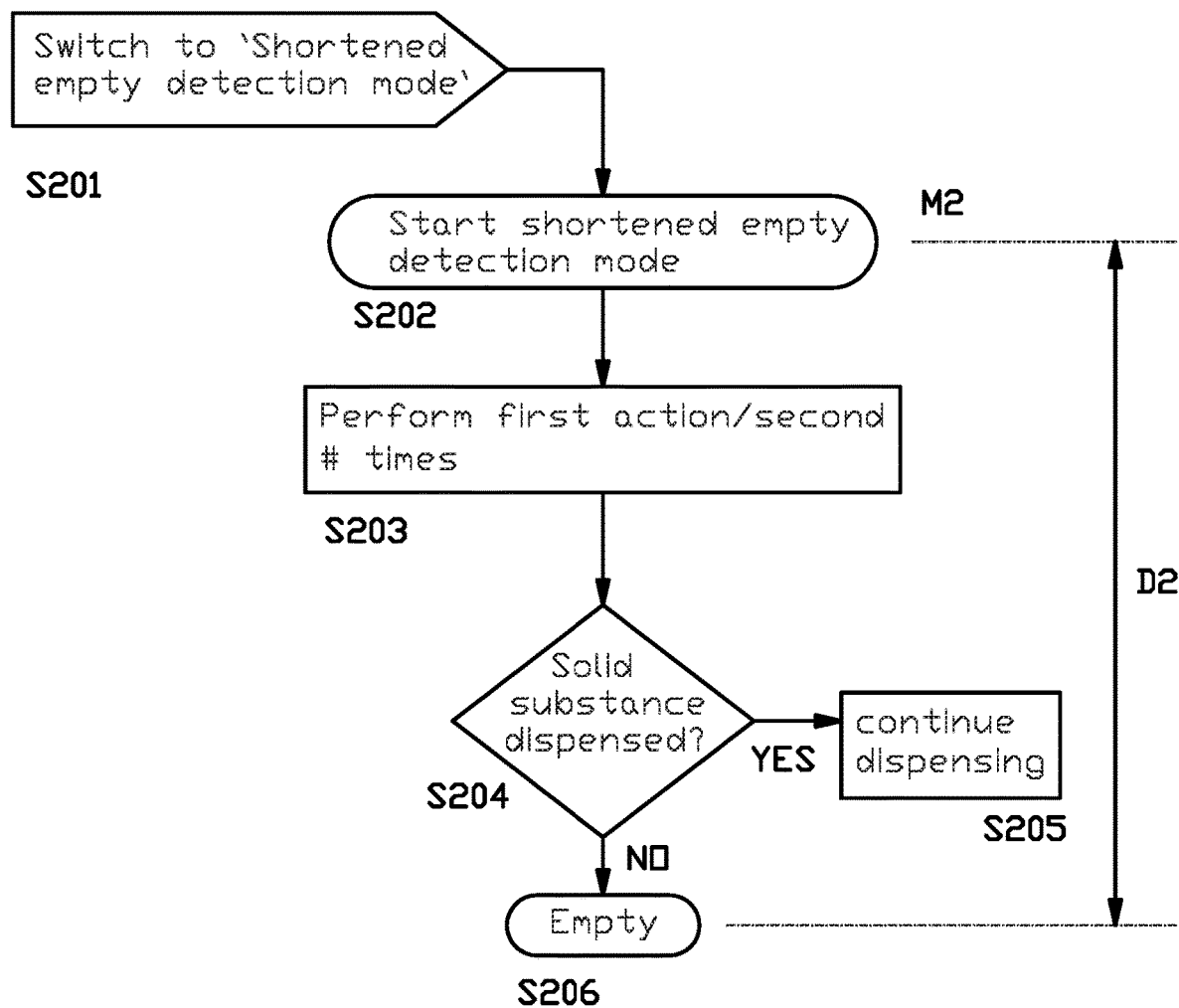

FIGS. 8A and 8B show a diagram of method for dispensing of the medicaments 90 from one of the feeder units 40, including steps for empty detection of said feeder units 40.

As shown in FIG. 8A, the method may be initiated when no dispense is detected at one of the feeder units 40, e.g. when no medicament 90 is fed from the container 50 towards the outlet 51 and/or detected at said outlet 51 when the dispensing mechanism 52 is operated (step S101). The processor 71 of the control unit 7, as shown in FIG. 1, starts a mode selection program (S102). The program involves a determination of a remaining value indicative of the amount of the medicaments 90 remaining in the container 50 of the feeder unit 40 that has experienced the dispensing failure (step S103).

The remaining value can be determined in a similar way to the determination of the depletion time 82 in FIG. 6, e.g. by a prediction and/or calculation based on a count since a start time or by detecting the actual amount with the one or more sensors 53, 54 at the feeder unit 40, as shown in FIG. 2A.

As further shown in FIG. 8A, the processor 71 compares the remaining value with a threshold value (step S104). The threshold value can be predetermined. The threshold value may be the same for every feeder unit 40, or it may be specific to each feeder unit 40. The threshold value may be expressed as a percentage of the volume of the container 50, a level within said container 50 or as an amount of the medicaments 90. The threshold value may for example be fifty percent of the original amount of the medicaments 90.

When the remaining value is greater than or above the threshold value, the processor 71 will select and/or start a complete empty detection mode M1 (step S105). The complete empty detection mode M1 includes performing a first action a first number of times or instances (step S106). The first action may for example be repeatedly controlling the dispensing mechanism 52. The first action may for example be performed ten times.

After each instance of the first action, or at the end of performing the first action for the given number of times or instances, a check is performed if a dispense is or has been detected (step S107). In the affirmative, normal dispensing may be continued or resumed (step S108). When still no dispense is detected, the complete empty detection mode M1 may further include the step of performing a second action a number of times or instances (S109). The second action may for example be a different way of dispensing, reversing the dispensing mechanism 52 or shaking of the feeder unit 40 with the use of the robotic manipulator 11.

Again, after each instance of the second action or at the end of performing the second action for the given number of times or instances, a check is performed if a dispense is or has been detected (step S110). Alternatively, depending on the type of the second action, the complete detection mode M1 may first include a repeat of steps S106 and S107, for example when the second action in itself is not a dispensing action (e.g. the shaking with the robotic manipulator).

When a dispense is detected after performing the second action, and optionally repeating the first action, the dispensing may be continued or resumed (step S111 or S108). When still no dispense is detected, it is assumed that the feeder unit 40 is empty (step S112) and appropriate action may be taken to supplement or replace the feeder unit 40, e.g. in accordance with any of the aforementioned methods.

From start (step S105) to the determination that the feeder unit 40 is empty (step S112), the complete empty detection mode M1 may take a relatively long time, represented by a first duration D1 in FIG. 8A. The first duration D1 may be more than fifteen seconds, more than twenty seconds or even more than thirty seconds. During this time, the first collection hopper 31 has to remain stationary below the feeder unit 40 that is being tested, to catch any medicaments 90 that are successfully dispensed during the complete empty detection mode M1. Hence, the complete empty detection mode M1 of a single feeder unit 40 is creating downtime in the dispensing operation of the entire dispensing device 1.

Hence, the processor 71 is configured or programmed to switch to or select a shortened empty detection mode M2 when the remaining value, as determined in step S103, is less than or below the threshold value (step S201).

The shortened empty detection mode M2 is shown in more detail in FIG. 8B. After selecting the shortened empty detection mode M2 (step S201), the processor 71 starts said shortened empty detection mode M2 (step S202).

The shortened empty detection mode M2 involves either performing the first action and the second action of the complete empty detection mode M1 for a second number of times or instances, less than the number of times or instances set for those actions in the complete empty detection mode M1, or performing only one of the first action or the second action for the same number of times or instances or a lesser number of times or instances (step S203). Step S203 may for example only involve operating the dispensing mechanism 52 of the affected feeder unit 40 for half the number of times or instances compared to step S106 in the complete empty detection mode M1. Also, the second action may be left out completely from the shortened empty detection mode M2 to save valuable time.

After each action in step S203, or after completing the action(s) of step S203 for the given number of times or instances, a check is performed to see if a medicament 90 is or has been dispensed (step S204). In the affirmative, the normal dispensing can be resumed or continued (step S205). If still no dispense is detected, it is assumed that the feeder unit 40 is empty (step S206) and appropriate action, similar to end of the complete empty detection mode, may be taken.

From start (step S202) to the determination that the feeder unit 40 is empty (step S206), the shortened empty detection mode M2 takes a relatively short time, represented by a second duration D2 in FIG. 8B. The second duration D2 may for example be less than half of the first duration D1, and preferably less than a quarter of the first duration Dl.

FIGS. 9A-9C show an alternative dispensing device 101 according to a second embodiment of the invention, which differs from the aforementioned dispensing device 1 in that the collection section 102 comprises an array of feeder positions 120 which are distributed along an alternative, non-circular collection path Z2. The collection path Z2 is endless, similar to the circular collection path Z1 of the first embodiment of the invention. The alternative collection path Z2 may comprises one or more circular and non-circular segments. In this example, the alternative collection path Z2 comprises two straight or linear segments and two semi-circular segments connecting the two straight or linear segments to endlessly connect the segments.

Similarly, the collection section 103 comprises a plurality of collection hoppers 31 configured to travel along the alternative collection path Z2 in the collection direction C between a start position A and an end position B, thereby visiting each feeder position 120 of the plurality of feeder positions 120 and collecting the required medicaments 90 from the feeder units 40 held in said plurality of feeder positions 120. The plurality of collection hoppers 31 may for example be arranged on an endless drive belt, chain 132 or the like driving the plurality of hoppers 31 in the collection direction C along the alternative collection path Z2.

The alternative dispensing device 101 further includes a packaging section 106 having a first packaging unit 61 positioned in a first packaging position P1 along the alternative collection path Z2.

FIG. 9A shows the first feeder unit 41 (see FIG. 9B) in a first feeder position 121 and the second feeder unit (see FIG. 9C) in a second feeder position 122 downstream from the first feeder position 121 in the collection direction C, in the same way as the relative positioning of the feeder units 41, 42 in the previously discussed embodiment.

A robotic manipulator 11 similar to the one shown in the previously discussed embodiment may be arranged at a center position within the alternative collection path Z2.

It will be clear that the dispensing operation and methods described in relation to the dispensing device 1 according to the first embodiment of the invention can be applied, mutatis mutandis, to the alternative dispensing device 101 according to the second embodiment of the invention.

While the description refers to medicaments, tablets, etc., the devices and methods could be used for dispensing other types of solid discrete items for separation and packaging.

It is to be understood that the above description is included to illustrate the operation of the embodiments and is not meant to limit the scope of the invention. From the above discussion, many variations will be apparent to one skilled in the art that would yet be encompassed by the spirit and scope of the present invention.

LIST OF REFERENCE NUMERALS 1 dispensing device
10 housing
11 robotic manipulator
12 stock position
2 dispensing section
20 array of feeder positions
21 first feeder position
22 second feeder position
23 prior feeder position
24 feeder loading member
25 feeder loading position
26 manual loading position
3 collection section
30 plurality of collection hoppers
31 first collection hopper
32 collection frame
40 plurality of feeder units
41 first feeder unit
42 second feeder unit
50 container
51 outlet
52 dispensing mechanism
53 verification sensor
54 count sensor
6 packaging section
61 first packaging unit
62 second packaging unit
7 control unit
71 processor
72 computer-readable medium
8 graphical user interface
80 timeline 81 notification
82 depletion time
83 due time
90 medicaments
91 medicaments of a first composition
101 alternative dispensing device
102 dispensing section
120 array of feeder positions
121 first feeder position
122 second feeder position
103 collection section
132 drive chain
106 packaging section
A start position
B end position
C collection direction
D1 first duration
D2 second duration
F packaged medicaments
G1 first set of dispensing instructions
G2 second set of dispensing instructions
G3 third set of dispensing instructions
H spacing angle
L logistical parameter
M1 complete empty detection mode
M2 shortened empty detection mode
P1 first packing position
P2 first packing position
R collection range
S1-S6 steps of a prioritization method
S101-S112 steps of a method for empty detection
S201-S206 further steps of the method for empty detection
t time
X rotation axis
Z1 endless collection path
Z2 alternative endless collection path

The invention claimed is:

1. A method for dispensing discrete medicaments (90) with a dispensing device (1, 101) comprising a dispensing section (2, 102), a collection section (3, 103) and a packaging section (6, 106), wherein the dispensing section (2, 102) defines an array of feeder positions (20, 120) distributed along an endless collection path (Z1, Z2) for holding a plurality of feeder units (40), wherein the collection section (3, 103) comprises a first collection unit (31) that is movable with respect to the array of feeder positions (20, 120) in a collection direction (C) along the endless collection path (Z1, Z2) between a start position (A) downstream from a first packing position (P1) in the collection direction (C) and an end position (B) at or near the first packing position (P1), wherein the method comprises the steps of:
positioning a first feeder unit (41) of the plurality of feeder units (40) at a first feeder position (21, 121) of the array of feeder positions (20, 120); and
prior to removing the first feeder unit (41) from the first feeder position (21, 121), positioning a second feeder unit (42) of the plurality of feeder units (40) at a second feeder position (22, 122) of the array of feeder positions (20, 120), downstream from the first feeder position (21, 121) in the collection direction (C),
wherein the first feeder unit (41) and the second feeder unit (42) hold medicaments (90) of the same first composition (91).

2. The method according to claim 1, wherein, when the first feeder unit (41) is empty or unable to dispense the medicaments (90) at the first feeder position (21, 121) into the first collection unit (31), the method further comprises the step of:
moving said first collection unit (31) in the collection direction (C) and dispensing the medicaments (90) from the second feeder unit (42) at the second feeder position (22, 122) into the first collection unit (31).

3. The method according to claim 1, wherein the method, prior to positioning of the first feeder unit (41) at the first feeder position (21, 121), the first feeder unit (41) was positioned at a prior feeder position (23) of the array of feeder positions (20, 120) downstream from said first feeder position (21, 121), wherein the method further comprises the steps of:
removing the first feeder unit (41) from the prior feeder position (23); and
moving said first feeder unit (41) from the prior feeder position (23) towards the first feeder position (21, 121).

4. The method according to claim 3, wherein the method further comprises the step of:
dispensing the medicaments (90) from the second feeder unit (42) at the second feeder position (22) into the first collection unit (31) during the moving of the first feeder unit (41) from the prior feeder position (23) towards the first feeder position (22, 122).

5. The method according to claim 1, wherein the first collection unit (31) is movable along the endless collection path (Z1, Z2) over a collection range (R) that starts at the start position (A) and that ends at the end position (B).

6. The method according to claim 5, wherein the first feeder position (21, 121) is located in a first half of the first collection range (R) considered from the start position (A).

7. The method according to claim 5, wherein the second feeder position (22, 122) is located in a second half of the collection range (R) considered from the start position (A).

8. The method according to claim 1, wherein the first feeder position (21, 121) and the second feeder position (22, 122) are spaced apart in the collection direction over a spacing angle (H) of at least five degrees.

9. The method according to claim 1, wherein the dispensing device (1, 101) comprises a robotic manipulator (11) and positioning and/or removing of the first feeder unit (41) and the second feeder unit (42) are performed with use of the robotic manipulator (11).

10. The method according to claim 1, wherein the endless collection path (Z1) is circular.

11. The method according to claim 10, wherein the array of feeder positions (20) is distributed circumferentially about a rotation axis (X) and wherein the first collection unit (31) is rotatable about said rotation axis (X) along the endless collection path (Z1).

12. The method according to claim 1, wherein the endless collection path (Z2) is non-circular.

13. A computer program product comprising a non-transitory computer-readable medium (72) holding instructions that, when executed by a processor (71), cause a dispensing device (1, 101) to perform the steps of the method according to claim 1.

14. A dispensing device (1, 101) for dispensing discrete medicaments (90),
the dispensing device (1, 101) comprising:
a dispensing section (2, 102) defining an array of feeder positions (20, 120) distributed along an endless collection path (Z1, Z2) for holding a plurality of feeder units (40), the array of feeder positions (20, 120) comprising at least a first feeder position (21, 121) and a second feeder position (22, 122), a collection section (3, 103) comprising a first collection unit (31) that is movable with respect to the array of feeder positions (20, 120) in a collection direction (C) along the endless collection path (Z1, Z2), a packaging section (6, 106) for packaging the medicaments (90) received from the collection section (3, 103), and a robotic manipulator (11) and a control unit (7) for controlling the robotic manipulator (11) to:

position a first feeder unit (41) at the first feeder position (21, 121); and prior to removing the first feeder unit (41) from the first feeder position (21, 121), positioning a second feeder unit (42) at the second feeder position (22, 122), the second feeder position (22, 122) located downstream from the first feeder position (21, 121) in the collection direction (C), wherein the first feeder unit (41) and the second feeder unit (42) hold medicaments (90) of the same first composition (91).

15. The dispensing device of claim 14, wherein the packaging section (6) comprises a first packaging unit (61) at or connecting to a first packing position (P1).

16. The dispensing device of claim 14, wherein the first collection unit (31) is movable between a start position (A) downstream of a first packing position (P1) in the collection direction (C) and an end position (B) at or near the first packing position (P1).

17. The dispensing device of claim 13, wherein the first collection unit (31) comprises a hopper.

18. The dispensing device according to claim 13, wherein the endless collection path (Z1) is circular.

19. The dispensing device according to claim 18, wherein the array of feeder positions (20) is distributed circumferentially about a rotation axis (X) and wherein the first collection unit (31) is rotatable about said rotation axis (X) along the endless collection path (Z1).

20. The method according to claim 13, wherein the endless collection path (Z2) is non-circular.

21. A method of continuously dispensing, collecting and packaging discrete medicaments (90) with a dispensing device comprising a dispensing section (2, 102), a collection section (3, 103), and a packaging section (6, 106), wherein the dispensing section (2, 102) comprises an array of feeder positions (20, 120) distributed along an endless collection path (Z1, Z2) for holding a plurality of feeder units (40), and the collection section (3, 103) comprises a first collection unit (31) that is movable with respect to the array of holding positions (20, 120) in a collection direction (C) along the endless collection path (Z1, Z2) to align with a plurality of the array of feeder positions (120), the method comprising:

placing a first feeder unit (41) at a first feeder position (21, 121) in the array of feeder positions (20, 120), placing a second feeder unit (42) at a second feeder position (22, 122) in the array of feeder positions (20, 120), the second holding position (22, 122) located downstream from the first holding position (21, 121);

dispensing the medicaments (90) from the first feeder unit (41) into the first collection unit (31);

moving the first collection unit (31) in the collection direction (C) to align with the second feeder unit (42) when the first feeder unit (41) is empty or no longer dispenses the medicament (90); and dispensing the medicaments (90) from the second feeder unit (42) into the first collection unit (31), wherein the first feeder unit (41) and the second feeder unit (42) contain medicaments (90) of the same first composition (91).

22. The method of claim 21, wherein the steps of placing the first and second feeders (41, 42) are done using a robot (11).

23. The method of claim 21, and further comprising transferring the medicament (90) from the first collection unit (31) to a first packaging unit (61) for packaging.

24. The method of claim 21, and further comprising:
removing and/or replacing the first feeder unit (41).

* * * * *